(12) United States Patent
Scott et al.

(10) Patent No.: US 8,557,298 B2
(45) Date of Patent: *Oct. 15, 2013

(54) MEDICAMENTS FOR CHEMOTHERAPEUTIC TREATMENT OF DISEASE

(75) Inventors: Timothy C. Scott, Knoxville, TN (US); H. Craig Dees, Knoxville, TN (US); Eric A. Wachter, Oak Ridge, TN (US)

(73) Assignee: Provectus Pharmatech, Inc., Knoxville, TN (US)

( * ) Notice: Subject to any disclaimer, the term of this patent is extended or adjusted under 35 U.S.C. 154(b) by 687 days.

This patent is subject to a terminal disclaimer.

(21) Appl. No.: 11/951,800

(22) Filed: Dec. 6, 2007

(65) Prior Publication Data

US 2008/0118567 A1   May 22, 2008

Related U.S. Application Data

(63) Continuation-in-part of application No. 09/900,355, filed on Jul. 6, 2001, now Pat. No. 7,648,695, and a continuation-in-part of application No. 09/130,041, filed on Aug. 6, 1998, now abandoned, and a continuation-in-part of application No. 09/635,276, filed on Aug. 9, 2000, now abandoned, which is a continuation-in-part of application No. 09/216,787, filed on Dec. 21, 1998, now Pat. No. 6,331,286, said application No. 09/900,355 is a continuation-in-part of application No. 09/799,785, filed on Mar. 6, 2001, now Pat. No. 7,390,668.

(60) Provisional application No. 60/218,464, filed on Jul. 14, 2000.

(51) Int. Cl.
  *A61K 33/42* (2006.01)
  *A61K 33/14* (2006.01)
  *A61P 35/00* (2006.01)

(52) U.S. Cl.
  USPC .......................................... 424/601; 424/680

(58) Field of Classification Search
  None
  See application file for complete search history.

(56) References Cited

U.S. PATENT DOCUMENTS

| | | |
|---|---|---|
| 3,563,750 A | 2/1971 | Walker et al. |
| 3,868,950 A | 3/1975 | Kato |
| 3,973,848 A | 8/1976 | Jowett et al. |
| 3,986,513 A | 10/1976 | Stuhl |
| 4,066,650 A | 1/1978 | Egyud |
| 4,172,979 A | 10/1979 | Morrison |
| 4,241,060 A | 12/1980 | Smithen |
| 4,282,232 A | 8/1981 | Agrawal |
| 4,320,140 A | 3/1982 | Crounse et al. |
| 4,371,540 A | 2/1983 | Lee et al. |
| 4,444,189 A | 4/1984 | Seiverd |
| 4,462,992 A | 7/1984 | Agrawal et al. |
| 4,490,543 A | 12/1984 | Bergquist et al. |
| 4,578,079 A | 3/1986 | Ruoslahti et al. |
| 4,589,881 A | 5/1986 | Pierschbacher et al. |
| 4,599,227 A | 7/1986 | Dees et al. |
| 4,647,578 A | 3/1987 | Crounse et al. |
| 4,652,562 A | 3/1987 | Berenyi nee Poldermann |
| 4,681,091 A | 7/1987 | Picker et al. |
| 4,691,332 A | 9/1987 | Burstein et al. |
| H505 H | 8/1988 | Slatkin et al. |
| 4,765,331 A | 8/1988 | Petruzzi et al. |
| 4,769,390 A | 9/1988 | Roelz et al. |
| 4,820,258 A | 4/1989 | Mondain-Monval |
| 4,822,335 A | 4/1989 | Kawai et al. |
| 4,846,789 A | 7/1989 | Heitz et al. |
| 4,856,528 A | 8/1989 | Yang et al. |
| 4,867,973 A | 9/1989 | Goers et al. |
| 4,880,821 A | 11/1989 | Saari |
| 4,897,423 A | 1/1990 | Saari et al. |
| 4,915,804 A | 4/1990 | Yates et al. |
| 4,921,589 A | 5/1990 | Yates et al. |
| 4,921,963 A | 5/1990 | Skov et al. |

(Continued)

FOREIGN PATENT DOCUMENTS

| | | |
|---|---|---|
| EP | 0049837 A1 | 4/1982 |
| EP | 0 097 012 | 6/1983 |

(Continued)

OTHER PUBLICATIONS

"Dacarbazine for Injection" package insert, Hospira, Inc., 2007, pp. 1-2.

(Continued)

*Primary Examiner* — Janet Epps-Smith
(74) *Attorney, Agent, or Firm* — Husch Blackwell LLP

(57) ABSTRACT

New chemotherapeutic medicaments and certain medical uses and methods for use of such chemotherapeutic medicaments for treatment of disease in human or animal tissue are described, wherein a primary active component of such medicaments is a halogenated xanthene or halogenated xanthene derivative. Preferably, the halogenated xanthene is Rose Bengal or a functional derivative of Rose Bengal. The halogenated xanthenes constitute a family of useful chemotherapeutic agents that afford selective, persistent accumulation in certain tissues. In preferred embodiments, such medicaments are used for treatment of a variety of conditions affecting the skin and related organs, the mouth and digestive tract and related organs, the urinary and reproductive tracts and related organs, the respiratory tract and related organs, the circulatory system and related organs, the head and neck, the endocrine and lymphoreticular systems and related organs, various other tissues, such as connective tissues and various tissue surfaces exposed during surgery, as well as various tissues exhibiting microbial or parasitic infection. In another preferred embodiment, such medicaments are produced in various formulations useful for intracorporeal or topical administration, including in liquid, semisolid, solid or aerosol delivery vehicles.

20 Claims, 4 Drawing Sheets

(56) References Cited

U.S. PATENT DOCUMENTS

| | | | |
|---|---|---|---|
| 4,925,736 A | 5/1990 | Shikowitz | |
| 4,927,941 A | 5/1990 | Kagiya et al. | |
| 4,945,102 A | 7/1990 | Suzuki et al. | |
| 4,954,515 A | 9/1990 | Suto | |
| 4,957,481 A | 9/1990 | Gatenby | |
| 4,973,848 A | 11/1990 | Kolobanov et al. | |
| 4,977,273 A | 12/1990 | Kagiya et al. | |
| 4,983,670 A | 1/1991 | Yates et al. | |
| 5,008,907 A | 4/1991 | Norman et al. | |
| 5,019,368 A | 5/1991 | Epstein et al. | |
| 5,026,694 A | 6/1991 | Skov et al. | |
| 5,034,613 A | 7/1991 | Denk et al. | |
| 5,036,089 A | 7/1991 | Suto | |
| 5,036,096 A | 7/1991 | Suto | |
| 5,053,006 A | 10/1991 | Watson | |
| 5,064,849 A | 11/1991 | Suzuki et al. | |
| 5,128,139 A | 7/1992 | Brown et al. | |
| 5,147,652 A | 9/1992 | Egyud | |
| 5,149,801 A | 9/1992 | Kahl et al. | |
| 5,151,096 A | 9/1992 | Khoury | |
| 5,162,218 A | 11/1992 | Schultz | |
| 5,175,287 A | 12/1992 | Lee et al. | |
| 5,215,738 A | 6/1993 | Lee et al. | |
| 5,219,346 A | 6/1993 | Wagnieres et al. | |
| 5,225,182 A | 7/1993 | Sharma | |
| 5,231,984 A | 8/1993 | Santana-Blank | |
| 5,258,453 A | 11/1993 | Kopecek et al. | |
| 5,270,330 A | 12/1993 | Suzuki et al. | |
| 5,284,831 A | 2/1994 | Kahl et al. | |
| 5,294,715 A | 3/1994 | Papadopoulou-Rosenzweig et al. | |
| 5,302,369 A | 4/1994 | Day et al. | |
| 5,304,654 A | 4/1994 | Kagiya et al. | |
| 5,342,959 A | 8/1994 | Beylin et al. | |
| 5,354,774 A | 10/1994 | Deckelbaum et al. | |
| 5,368,031 A | 11/1994 | Cline et al. | |
| 5,409,483 A | 4/1995 | Campbell et al. | |
| 5,445,608 A | 8/1995 | Chen et al. | |
| 5,457,183 A | 10/1995 | Sessler et al. | |
| 5,462,053 A | 10/1995 | Briggs et al. | |
| 5,468,234 A | 11/1995 | Griffin et al. | |
| 5,481,000 A | 1/1996 | Beylin et al. | |
| 5,498,694 A | 3/1996 | Ruoslahti | |
| 5,514,707 A | 5/1996 | Deckelbaum et al. | |
| 5,543,527 A | 8/1996 | Beylin et al. | |
| 5,552,452 A | 9/1996 | Khadem et al. | |
| 5,556,992 A | 9/1996 | Gaboury et al. | |
| 5,558,666 A | 9/1996 | Dewey et al. | |
| 5,567,765 A | 10/1996 | Moore et al. | |
| 5,571,152 A | 11/1996 | Chen et al. | |
| 5,573,773 A | 11/1996 | Kis et al. | |
| 5,575,756 A | 11/1996 | Karasawa et al. | |
| 5,576,013 A * | 11/1996 | Williams et al. | 424/423 |
| 5,579,773 A | 12/1996 | Vo-Dinh et al. | |
| 5,586,981 A | 12/1996 | Hu | |
| 5,590,660 A | 1/1997 | MacAulay et al. | |
| 5,591,422 A | 1/1997 | Hemmi et al. | |
| 5,599,923 A | 2/1997 | Sessler et al. | |
| 5,601,802 A | 2/1997 | Hemmi et al. | |
| 5,602,142 A | 2/1997 | Papadopoulou-Rosenzweig | |
| 5,616,584 A | 4/1997 | Lee et al. | |
| 5,622,699 A | 4/1997 | Ruoslahti et al. | |
| 5,622,946 A | 4/1997 | Sessler et al. | |
| 5,624,925 A | 4/1997 | Lee et al. | |
| 5,627,263 A | 5/1997 | Ruoslahti et al. | |
| 5,629,291 A | 5/1997 | Ruoslahti et al. | |
| 5,632,970 A | 5/1997 | Sessler et al. | |
| 5,641,764 A | 6/1997 | Martin et al. | |
| 5,645,816 A | 7/1997 | Unger | |
| 5,647,368 A | 7/1997 | Zeng et al. | |
| 5,654,267 A | 8/1997 | Vuori et al. | |
| 5,654,423 A | 8/1997 | Kahl et al. | |
| 5,659,048 A | 8/1997 | Beylin et al. | |
| 5,667,764 A | 9/1997 | Kopia et al. | |
| 5,674,183 A | 10/1997 | Adachi | |
| 5,676,928 A | 10/1997 | Klaveness et al. | |
| 5,693,015 A | 12/1997 | Walker et al. | |
| 5,700,825 A | 12/1997 | Hofer et al. | |
| 5,702,683 A | 12/1997 | Smith et al. | |
| 5,706,810 A | 1/1998 | Rubinsky et al. | |
| 5,709,653 A | 1/1998 | Leone | |
| 5,728,090 A | 3/1998 | Martin et al. | |
| 5,733,572 A | 3/1998 | Unger et al. | |
| 5,747,064 A | 5/1998 | Burnett et al. | |
| 5,773,460 A | 6/1998 | Gaboury et al. | |
| 5,780,052 A | 7/1998 | Khaw et al. | |
| 5,780,653 A | 7/1998 | Tao et al. | |
| 5,807,231 A | 9/1998 | Liprie | |
| 5,827,186 A | 10/1998 | Chen | |
| 5,829,448 A | 11/1998 | Fisher et al. | |
| 5,830,526 A | 11/1998 | Wilson et al. | |
| 5,832,931 A | 11/1998 | Wachter et al. | |
| 5,837,677 A | 11/1998 | Horwitz et al. | |
| 5,913,884 A | 6/1999 | Trauner et al. | |
| 5,935,942 A | 8/1999 | Zeimer | |
| 5,968,479 A | 10/1999 | Ito et al. | |
| 5,998,597 A | 12/1999 | Fisher et al. | |
| 6,013,053 A | 1/2000 | Bower et al. | |
| 6,036,941 A * | 3/2000 | Bottiroli et al. | 424/9.6 |
| 6,042,603 A | 3/2000 | Fisher et al. | |
| 6,274,614 B1 | 8/2001 | Richter et al. | |
| 6,331,286 B1 | 12/2001 | Dees et al. | |
| 6,991,776 B2 | 1/2006 | Dees et al. | |
| 7,353,829 B1 | 4/2008 | Wachter | |
| 7,384,623 B1 * | 6/2008 | Dees et al. | 424/9.37 |
| 7,390,668 B2 * | 6/2008 | Dees et al. | 436/124 |
| 7,648,695 B2 * | 1/2010 | Dees et al. | 424/9.37 |
| 2002/0001567 A1 | 1/2002 | Dees et al. | |

FOREIGN PATENT DOCUMENTS

| | | |
|---|---|---|
| EP | 0146059 A2 | 6/1985 |
| EP | 0 175 617 | 9/1985 |
| EP | 0175617 A | 3/1986 |
| EP | 0504761 A1 | 9/1992 |
| EP | 0471794 B1 | 10/1996 |
| EP | 0631610 B1 | 6/1997 |
| EP | 0652709 B1 | 3/1999 |
| JP | 01-229087 | 12/1989 |
| JP | 06-128128 | 10/1994 |
| WO | WO 90/13296 | 11/1990 |
| WO | WO 93/21992 | 11/1993 |
| WO | WO 95/02324 A | 1/1995 |
| WO | WO 96/07431 | 3/1996 |
| WO | WO 97/03697 | 2/1997 |
| WO | WO 97/26920 | 7/1997 |
| WO | WO 97/39064 A1 | 10/1997 |
| WO | WO 97/40829 | 11/1997 |
| WO | WO 98/22184 | 5/1998 |
| WO | WO 98/37456 | 8/1998 |
| WO | WO 00/02576 | 1/2000 |
| WO | WO 00/07515 A | 2/2000 |
| WO | WO 00/25665 A | 5/2000 |
| WO | WO 00/25819 | 5/2000 |
| WO | WO 00/25829 | 5/2000 |
| WO | WO 00/37927 A | 6/2000 |
| WO | WO 01/72301 | 10/2001 |
| WO | WO 01/76595 | 10/2001 |

OTHER PUBLICATIONS

"Temodar® (temozolomide) Capsules, Temodar (temozolomide) for Injection," package insert, Schering-Plough, copyright 1999, 2008, 2005 (revised Apr. 2009), pp. 1-12.

US Label Information for "Yervoy™" revised Mar. 2011, pp. 1-20.

US Label Information for "Intron® A," Physician's Desk Reference, PDR Electronic Library, Jun. 19, 2006, pp. 1-31. http://www.thomsonhc.com/pdrel/librarian/ND_PR/Pdr/PFPUI/XU4KP3ClmVunrH/DDAK/.

Singer, J., "Partition Coefficients for Rose Bengal Drug Substance in 1-Octanol and Saline," Provectus Pharmaceuticals, Inc., Study No. 080707.01C, Jul. 18, 2008, pp. 1-4 (and attachments, pp. 1-5).

Wachter, E. et al., Imaging Photosensitizer Distribution and Pharmacology using Multiphoton Microscopy, Functional Imaging and

(56) References Cited

OTHER PUBLICATIONS

Optical Manipulation of Living Cells and Tissues, (2002), SPIE Paper 4622A-14, BiOS 2002 (Biomedical Optics), San Jose, CA, Jan. 24, 2002.
Andreoni, A., et al., (1982) Two-step lazer activation of hematoporphyrin derivative. Chem. Phys. Lett, 8 8, 37-39.
Bodaness, R.S. and King, D.S. (1985) The two-photon induced fluorescence .of the tumor localizing photo-sensitizer hematoporphyrin derivative via 1064 rm . . . Biochem. Biophys.
Bodaness, R.S., et al., (1986) Two-photon laser-induced fluorescence of the tumor-localizing photosensitive hematoporphyrin derivative. J. Biol. Chem. 2 6 1, 12098-12101.
Chan, C.K. and Sari, S.O. (1974) Tunable dye laser pulse converter for production of picosecond pulses. App. Phys. Lett. 2 5, 403-406.
Cheong, W-F. et al., "A Review of the Optical Properties of Biological Tissues," IEEE 5.Quant. Election 2 6, 2166-2185 (1990).
Cimino., G.D., et al., (1985) Psoralens as photoactive probes of nucleic acid structure and function: organic chemistry, photochemistry, and biochemistry. Ann. Rev. Biochem.
Dagani, R., (1996) Two photons shine in 3-D data storage. Chem Eng. News, Sep. 23, 1996, 68-70.
Dougherty, T.J., et al., "Photoradiation Therapy II Cure of Animal Tumors With Hematoparphyrin and Light," J.Nat'l Cancer-Inst. 5 5, 115-120 (1975).
Dolphin, D., (1994) 1993 Syntex award lecture, photomedicine and photodynamic therapy. Can. J. Chem. 7 2 1005-1013.
Draumer, N.H., et al., (1997) Femtosecond dynamics of excited-state evolution in [Ru(bpy)3]2+. Science 2 7 5, 54-57.
Fisher, W.G., et al., (1997) Two-photon spectroscopy and photochemistry of tris (2,2'-bipyridine)-0ruthenium(II). J. Phys. Chem. (in press).
Fugishima, I., et al., (1991) Photodynamic therapy using phophorbide a and ND:YAG laser. Neurol. Med. Chir. (Tokyo) 3 1, 257-263.
Georges, J., et al., (1996) Limitations arising from optical saturation in fluorescence and thermal lens spectrometries using . . . App. Spectrosc. 5 0, 1505-1511.
Gomer, C.J., et al., (1989) Properties and applications of photodynamic therapy. Rad. Res. 1 2 0, 1-18.
Göpert-Mayer, M., (1931) Elementary process with two quantum jumps. Ann. Physik 9, 273-294.
Hammer, D.X., et al., (1996) Experimental investigation of ultrashort pulse laser-induced breakdown thresholds in aqueous media. Ieee J. Quant. Electron. 3 2, 670-678.
Harris, J.M., et al., (1975) Pulse generation in cw-dye laser by mode-locked synchronous pumping. App. Phys. Lett. 2 6, 16-18.
Hermann, J.P. and Ducuing, J. (1972) Dispersion of the two-photon cross section in thodamine dyes. Opt. Comm. 6, 101-105.
Inaba, H., et al., (1985) Nd:YAG laser-induced hematoporphyrin visible fluorescence and two photon-excited . . . J. Opt. Soc. Am. A:Opt. lnage Science 2, p. 72 (mtg abst).
International Search Report for Application No. PCT/US99/17515, dated Oct. 25, 1999.
Kaiser, W. and Garrett, C.G.B., (1961) Two photon excitation in CaF2:Eu2+. Phys. Rev. Lett. 7, 2929-231.
Kennedy, S.M. and Lytle, F.E. (1986) p-Bis (o-methylstryl) benzene as a power-squared sensor for two-photon absorption measurement between 537 and 694 rm. Anal. Chem. 5 8, 26.
Kessel, D., et al., (1991) Photophysical and photobiological properties of diporphyrin ethers. Photochem. Photobiol. 5 3, 469,474.
Lenz, P. (1995) In vivo excitation of photosensitizers by infrared light. Photochem. Photobiol. 6 2, 333-338.
Lytle, F.E., (1981) Laser fundamentals. In Lasers in Chemical Analysis (Ed.: G.M.Hieftje,et al.) 5-6. The Humana Press, New Jersey.
Lytle, F.E., et al., (1980) Two-photon excitation of polycyclic aromatic hydrocarbons. Intern. UJ. Environ. Anal. Chem. 8, 303-312.
Marchesini, R., et al., (1986) A study on the possible involvement of nonlinear mechanism of light absorption by HpD with Nd:YAG laser. Lasers Surg. Med. 6, 323-327.

Mashiko, D., et al., (1985) Basic study on photochemical effect of pheophorbide-a irradiated by Nd:YAG laser light. Nippon Laser Igakukaishi 6, 113-116.
Mashiko, S., et al., (1986) Two-photon excited visible fluorescence of hematoporphyrin and phiophorbide a and in vitro experiments of the photodynamic . . . J. Opt. Soc. Am. B:Opt.
McClain, W.M., (1974) Two-photon molecular spectroscopy. Acc. Chem. Res. 7 129-135.
McClain, W.M. (1971) Excited state symmetry assignment through polarized two-photon absorption studies of fluids. J. Chem. Phys. 5 5, 2789-2796.
Mello, R.S., et al., "Radiation Dose Enhancement in Tumors with Iodine," Medical Physics, vol. 1, No. 1, pp. 75-78, Jan./Feb. 1983.
Monson, P.R. and McClain, W.M. (1970) Polarization dependence of the two-photon absorption of tumbling molecules . . . J. Chem. Phys. 5 3, 29-37.
Moscatelli, F.A., (1985) A Simple Conceptual Model for Two-Photon Absorption. Am. J. Phys. 5 4, 52-54.
Niemz, M.H., (1995) Threshold dependence of laser-induced optical breakdown on pulse duration. Appl. Phys. Lett. 6 6, 1181-1183.
Norman, A., et al., "X-Ray Phototherapy for Canine Brain Masses," Radiation Oncology Investigations, vol. 5, pp. 8-14, 1997.
Oh, D.H., et al., (1997) Two-photon excitation of 4'-hydroxymethyl-4,5', 8-trimethylpsoralen. Photochem. Photobiol. 6 5, 91-95.
Patrice, T., et al., (1983) Neodymium-yttrium aluminum garnet laser destruction of nonsensitized and hematoporphyrin derivative-sensitized tumors. Canc. Res. 4 3, 2876-2879.
Peticolas, W.L., (1967) Multiphoton spectroscopy. Ann. Rev. Phys. Chem. 1 8, 233-260.
Prasad, P.N. and He, G.S., (1996) Multiphoton resonant nonlinear-optical processes in organic molecules ACS Symposium Series 6 2 8, 225-236.
Shea, C.R., et al., (1990) Mechanistic investigation of doxycyckine photosensitization by picosecond-pulsed . . . J. Biol. Chem. 2 6 5, 5977-5982.
Song, P.S. and Tapley, K.J., Jr. (1979) Photochemistry and photobiology of psoralens. Photochem. Photobiol. 2 9, 1177-1197.
Spence, D.E., et al., (1991) 60-fsec pulse generation from a self-mode-locked Ti:Sapphire laser. Opt. Lett. 1 6, 42-44.
Steil, H., et al., (1993) Photophysical properties of the photosensitizer phophorbide a studied at high photon flux densities. J. Photochem. Photobiol. B: Biology 1 7, 181-18.
EP 0192 0579 Supplementary Partial European Search Report dated Apr. 23, 2004.
Swofford, R.L. and McClaim, W.M., 1975) The effect of spatial and temporal laser beam characteristics on two-photon absorption. Chem. Phys. Lett. 3 4, 455-459.
Wachter, E.A., Fisher et al., "Titanium: Sapphire Laser as an Excitation Source in Two-Photon Spectroscopy," Applied Spectroscopy, vol. 51, No. 2, pp. 218-226 (1997).
Wilson, B.C. and Patterson, M.S., (1986) The physics of photodynamic therapy. Phys. Med. Biol. 3 1, 327-360.
Yamashita, Y., et al., (1991) Photodynamic therapy using pheophorbide-a and Q-switched Nd:YAG laser on implanted human hepatocellular carcinoma. Gast. Jap. 2 6, 623-627.
Bertino, J.R., et al., "Part XIV: Oncology, The Principles of Cancer Therapy" Cecil Textbook of Medicine, Goldman, L., et al., eds. 21st Ed., W.B. Saunders Co., Philadelphi, Nov. 1999.
Diwu et al., "Phototherapeutic potential of alternative photosensitizers to porphyrins," Pharmac. Ther., 63 (1994) 1-35.
Heitz et al., "Photodegradation of halogenated xanthene dyes," Mississippi Agriculture and Forestry Experiment Station (MAFES), Publication 8532, 35-48, Publication Date: Jun. 30, 1978.
Kalka et al., "Photodynamic therapy in dermatology," J.Am. Acad. Derm., 42 (2000) 389-413.
Merck Index (1983) Windholz et al. (eds), p. 8183.
U.S. Appl. No. 09/096,832 to Wachter, et al., filed Jun. 12, 1998, including specification, claims, abstract drawings and PTO filing receipt.
Von Tappeiner et al., "Therapeutische versuche mit flouresszierenden Stoffen (Therapeutic experiments with flourescent substances)", Munch. Med. Wochenschr., 47 (1903) 2042-204.
Search Report re: PCT/US01/08924. Dated Jun. 22, 2001.

(56) References Cited

OTHER PUBLICATIONS

U.S. Appl. No. 09/382,622, filed Aug. 25, 1999, Dees.
U.S. Appl. No. 09/799,785, filed Mar. 6, 2001, Dees.
U.S. Appl. No. 09/817,448, filed Mar. 26, 2001, Dees.
U.S. Appl. No. 09/900,355, filed Jul. 6, 2001, Dees.
U.S. Appl. No. 10/331,854, filed Dec. 30, 2002, Dees.
U.S. Appl. No. 10/999,313, filed Nov. 30, 2004, Dees.
U.S. Appl. No. 11/124,654, filed May 9, 2005, Dees.
Amato, "Hope for a Magic Bullet That Moves at the Speed of Light," Science 262:32-33, Oct. 1, 1993.
Aungst, B.J., "Fatty Acids as Skin Permeation Enhancers," Percutaneous Penetration Enhancers, 1995, pp. 277-287, CRC Press, Inc., Boca Raton, FL.
Barr, H., et al., "Eradication of High-Grade Dysplasia in Columnar-Lined (Barrett's) Oesophagus by Photodynamic Therapy with Endogenously Generated Protoporphyrin IX," Lancet, Aug. 1996.
Bays, et al., "Light Dosimetry for Photodynamic Therapy in the Esophagus," Lasers in Surgery & Medicine, vol. 20, 290-303, 1997.
Bernhard, E.J., et al., "Re-Evaluating Gadolinium(III) Texaphyrin as a Radiosensitizing Agent," Cancer Research, vol. 60, pp. 86-91, Jan. 2000.
Bezman, et al., "Photodynamic Inactivation of E. coli by Rose Bengal Immobolized on Polystyrene Beads," Photochemistry and Photobiology, vol. 28, pp. 325-329 (1978).
Biddlestone, et al, "The Histopathology of Treated Barrett's Esophagus," Am J Surg Pathol, vol. 22, No. 2, 239-245, 1998.
Bottiroli, G., Croce, AC, Enzyme-Assisted Cell Photosensitization, Photochem Photobiol Sep. 1997; 66(3):374-83.
Budavari, S., ed., et al., The Merck Index, Merck & Co., Inc., 11th Ed., p. 4943, 1989.
Castro, et al., "The Concept of Laser Phototherapy," Laser Applications in Otolaryngology 29(b):1011-29, (1996).
Chattaraj, S.C. and Walker, R.B., "Penetration Enhancer Classification," Percutaneous Penetration Enhancers, 1995, pp. 5-20, CRC Press.
Chen, Sun-Yung, et al., "Theory of Two-Photon Induced Fluorescence Anisotropy Decay in Membranes," Biophys. J. Biophysical Society, vol. 64, pp. 1567-1575 (May 1993).
Definition of "Photodynamic," Merriam-Webster Dictionary, electronic edition, http://www.m-w.com/cgi-bin/dictionary, printed Sep. 4, 2003.
Definition of "Photosensitize," Merriam-Webster Dictionary, electronic edition, http:/www.m-w.com/cgi-bin/dictionary, printed Sep. 30, 2003.
Delpat, et al., "A New Liver Function Test: The Elimination of Rose Bengal When Injected Into the Circulation of Human Subjects," Arch. Intern. Med., vol. 34, pp. 533-541,1924.
Engelstad, et al., "Contrast Agents," Magnetic Resonance Imaging, Chapter 9, pp. 161-181, 215-219 (1988).
Ferguson, et al., "Resection for Barrett's Mucosa with High-Grade Dysplasia: Implications for Prophylactic Photodynamic Therapy," Journal of Thoracic & Cardiovascular Surgery, (1997).
Fisher, et al., "Clinical and Preclinical Photodynamic Therapy," Lasers in Surgery and Medicine, vol. 17, pp. 2-31, 1995.
Fluhler, et al., "Laser Intensity and Wavelength Dependence of Rose-Bengal-Photosensitized Inhibition of Red Blood Cell Acetylcholinesterase," Biochemica et Biophysica Acta, 9 (1989).
Hearst, J.E., et al., "The Reaction of the Psoralens with Deoxyribonucleic Acid," Quarterly Review of Biophysics, 17 (1984) 1-44.
http://eosweb.larc.nasa.gov/EDDOCS/Wavelengths_for_Colors. html; (2006) Responsible NASA Official: Michelle T. Ferebee.
Huang, et al., "Photothrombosis of Corneal Neovascularization by Intravenous Rose Bengal and Argon Laser Irradiation," Arch Opthaimol., vol. 106, pp. 680-685 (1988).
Iwamoto, K.S., et al., "Radiation Dose Enhancement Therapy with Iodine in Rabbit VX-2 Brain Tumors," Radiation Therapy and Oncology, vol. 8, pp. 161-170, 1987.
Johnson, Philip M., "The Multiphoton Ionization Spectrum of Benzene," Journal of Chemical Physics, vol. 64, No. 10, 4143-4148 (May 1976).
Joshi, et al., "The Role of Active Oxygen (1O2 and O2) Induced by Crude Coal Tar and its Ingredients Used in Photochemotherapy of Skin Diseases," 1984.
Katsumi, et al., "Photodynamic Therapy with a Diode Laser for Implanted Fibrosarcoma in Mice Employing Mono-L-Aspartyl Chlorin E6", Photochemistry and Photobiology (1996).
Kennedy, J.C., et al., "Photodynamic Therapy With Endogenous Protoporphyrin IX: Basic Principles and Present Clinical Experience," J. of Photochemistry and Photobiology, B: B, (1990).
Kozhn, Kaf. Ven. Bol., II Med. Inst., Moscow, Treatment of psoriasis with ultraviolet irradiation in combination with 1% alcohol solution of eosin, Elsevier Science B.V., Ams, (1978).
Kung-Tung, et al., "Therapeutic Effects of Photosensitizer in Combination with Laser and ACNO on an in Vivo or in Vitro Model of Celebral Glioma," Chinese Medical Journal 108(, 1995.
Kurebayahi, et al. (English Translation of Abstract) The Journal of Toxicological Sciences, May 1988. vol. 13. No. 2, pp. 61-70.
Lakowicz, Joseph R., et al., "Two-Color Two-Photon Excitation of Fluorescence," Photochemistry and Photobiology, pp. 632-635 (1996).
Lauffer, et al., "MRI Contrast Agents; Basic Principles and Organ- and Tissue-Directed MRI Contrast Agents," MRI Clinical Magnetic Resonance Imaging, Second Edition, vol. O, 1996.
Lindman, et al., "General Properties of Halogens and Static Parameters," Chlorine, Bromine and Iodine NMR—Physioco-Chemical and Biological Applications, pp. 1-5 (1976).
Marcus, et al., "Photodynamic Therapy for the Treatment of Squamous Cell Carcinoma Using Benzoporphyrin Derivative," J. Dermatol Sung Oncol 20:375-382, 1994.
Matsudaira, H., et al., "Iodine Contrast Medium Sensitizes Cultured Mammalian Cells to X Rays but not to Gamma Rays," Radiation Research, vol. 84, pp. 144-148, 1980.
Merck Index, 12th edition, 1996, entry Nos. 5055, 5068, 5069 and 5071.
Miller, R.W., et al., "Evaluation of Incorporated Iododeoxyuridine Cellular Radiosensitization by Photon Activation Therapy," Int. J. Radiation Oncology, Biol. Phys., vol. 13, 1987.
Neckers, D.C., Rose Bengal, Journal of Photochemistry and Photobiology, A: Chemistry: 47, pp. 1-29 (1989).
Nieman, George C., et al., "A New Electronic State of Ammonia Observed by Multiphoton Ionization," J. Chem. Phys. 68(12), pp. 5656-5657 (1978).
Norman, A., et al., "Iodinated Contrast Agents for Brain Tumor Localization and Radiation Dose Enhancement," Invest. Radiol., vol. 26, pp. s120-s1221, 1991.
Norman, A., et al., "Point/Counterpoint: Radiation Doses in Radiation Therapy are not Safe," Med. Phys. vol. 24 (11), pp. 1710-1713, Nov. 1997.
Norman, A., et al., "X-Ray Phototherapy for Solid Tumors," Acad Radiol, vol. 5, (Suppl 1), pp. s177-s179, Apr. 1998.
Overholt, et al., "Photodynamic Therapy for Barrett's Esophagus: Clinical Update," AJG, vol. 91, No. 9, 1719-1723, 1996.
Overholt, et al., "Photodynamic Therapy for Barrett's Esophagus: Cardiac Effects," Lasers in Surgery & Medicine, vol. 21, No. 5, 824-829, Nov. 1997.
Paddock Laboratories, Inc., "Paddock Compounding Vehicles," pp. 1-3, http://www.paddocklabs.com/compound/vehiclbb.html, 1997.
Pfeffer, W.D., et al., "Laser Two-Photon Excited Fluorescence Detector for Microbore Liquid Chromatography," Analytical Chemistry, 58 (1986) 2103-2105.
The Photonics Dictionary 2000, Book 4, 46th Edition, pp. D-105 and D-108, Laurin Publishing, Pittsfield, MA.
The Photonics Dictionary, 2003 Book 4, 49th edition of The Photonics Directory, Laurin Publishing, Pittsfield, MA, www.photonics. com, pp. D-104-D106, (2003).
Pierce, Jr. et al., "Conspectus," Comprehensive Therapy 16(4):3-8, 1990.
Rosenthal, et al., "Clinical Application of Photodynamic Therapy," Ann Med. 26:405-9, (1994).

(56) References Cited

OTHER PUBLICATIONS

RTEC Entry Nos. WN2817000 (N-Iodosucfcinimide) and PB7000000 (Iodoform), (2001).
Rubin, D., et al., "Nanoparticulate Contrast Media, Blood-Pool and Liver-Spleen Imaging," Investigative Radiology, vol. 29, Suppl. 2, pp. s280-s283, 1994.
Schmidt-Erfurth, et al., "Photodynamic Therapy of Experimental Choroidal Melanoma Using Lipoprotein-delivered Benzoporphyrin," Opthalmology 101:89-99, (1994).
Sepaniak, M.J., et al., "High-Performance Liquid Chromatographic Studies of Coal Liquids by Laser-Based Detectors," J. of Chromatography, 211 (1981) 95-102.
Sepaniak, M.J., et al., "Laser Two-Photon Excited Molecular Fluorescence Detection for High Pressure Liquid Chromatography," Analytical Chemistry, 49 (1977) 1554-1556.
Serafini, et al., "Iodine-123-Rose Bengal: An Improved Hepatobiliary Imagine Agent," Journal of Nuclear Medicine, 1990.
Shi, J., Xanthenes: Fluorone Derivatives, The Journal of Organic Chemistry 57 Jul. 31, 1992, No. 16, Washington, DC, pp. 4418-4421.
Smith, E.W. and Maibach, H.I., "Percutaneous Penetration Enhancers: The Fundamentals," Percutaneous Penetration Enhancers, 1995, pp. 1-4, CRC Press, Inc., Boca Raton, Florida.
Stables, G.I., "Photodynamic Therapy, Antitumour Treatment," Cancer Treatment Reviews, vol. 21, pp. 311-323, 1995.
Streitwieser, Jr., et al., "Benzene and the Aromatic Ring," Introduction to Organic Chemistry, Second Edition, Chapter 22, pp. 652-656 (1976).
Tessman, J.W., et al., "Photochemistry of Furan-Side 8-Methoxpsoralen-Tymidine Monoadduct Inside the DNA Helix, Conversion to Diadduct and to Pyrone-Side Monoadduct," Biochemi, (1985).
Teuchner, K, et al., "Spectroscopic Properties of Potential Sensitizers for New Photodynamic Therapy Start Mechanisms via Two-Step Excited Electronic States," Photochemistry, (1995).
Valenzeno, Dennis P. and Pooler, John P., Cell membrane Photomodification: Relative Effectiveness of Halogenated Fluoresceins for Photohemolysis, Photochemistry and Photobio, (1982).
Wilson, "Rose Bengal Staining of Epibulbar Squamous Neoplasms," Opthalmic Surgery, vol. 7, pp. 21-23, 1976.
Wirth, M.J., et al., "Two-Photon Excited Molecular Fluorescence in Optically Dense Media," Analytical Chemistry, 49 (1977) 2054-2057.
Wirth, M.J., et al., "Very High Detectability in Two-Photon Spectroscopy," Analytical Chemistry, 62 (1990) 2103-2105.
Young, A.R., "Photocarcinogenicity of Psoralens Used in PUVA Treatment: Present Status in Mouse and Man," J. of Photochemistry and Photobiology, B: Biology, 6 (1990) 237-247.
Young, S., et al., "Gadolinium (III) Texaphyrin: A Rumor Selective Radiation Sensitizer that is Detectable by MRI," Proc. Natl. Acad. Sci., vol. 93, pp. 6610-6615, Jun. 1996.
Zajusz, A., et al., "Normobaric Oxygen as a Sensitizer in Radiotherapy for Advanced Head and Neck Cancer," Neoplasm, vol. 42, No. 3, pp. 137-140, 1996.
Johansson, S., "Analysis and Purification of Rose Bengal Sodium for Use as Reference Substance and in Pharmaceutical Preparations," Svensk Farmaceutisk, (1973).
Amendment C After Final of U.S. Appl. No. 10/999,313, filed Jan. 23, 2008.
Amendment G of U.S. Appl. No. 09/382,622, filed Jul. 12, 2007.
Amendment G of U.S. Appl. No. 09/799,785, filed Jul. 24, 2007.
Amendment J After Final of U.S. Appl. No. 09/835,276, filed Oct. 15, 2007.
American Cancer Society, "What is Chemotherapy?" page from website, http://www.cancer.org.docroot/ETO/eto_1_3_Chemotherapy Principles.asp; printed Sep. 11, 2003.
Preliminary Examination Report PCT/US01/21585 dated Sep. 19, 2002.
Claims of U.S. Appl. No. 11/715,780, filed Mar. 8, 2008 and the Filing Receipt for this application dated May 30, 2007.
Claims of U.S. Appl. No. 11/936,963, filed Nov. 8, 2007 and the Filing Receipt for this application dated Feb. 15, 2008.
Definition of "Chemotherapeutic," Merriam-Webster Dictionary, electronic ed., http://www.m-w.com/cgi-bin/dictionary, printed Sep. 22, 2003.
Definition of "Chemotherapy," Merriam-Webster Dictionary, electronic ed., http://www.m-w.com/cgi-bin/dictionary, printed Sep. 22, 2003.
European Search Report dated Apr. 21, 2004 for EP 01 95 4627.
Green, Floyd J., The Sigma-Aldrich Handbook of Stains, Dyes and Indicators, Aldrich Chemical Company, Inc., Milwaukee, WI, pp. 304-305, pp. 320-321, pp. 636-637 (1990).
Niemz, M., "Laser-Tissue Interactions Fundamental and Applications," Springer-Verlang Berlin Heidelberg 1996; Library of Congress Cataloging-in-Publication Data applied for.
Preliminary Amendment A of U.S. Appl. No. 11/429,742, filed May 8, 2006.
Search Report re: PCT/US01/21585. Dated Oct. 18, 2001.
The Society of Dyers and Colourists, "Colour Index—Third Edition", 1971, p. 4417-4430, vol. 4, Bradford Yorkshire, England.
Simone, J.V., et al., "Part XIV: Oncology," Cecil Textbook of Medicine, Goldman, L., et al., eds. 21st Ed., W.B. Saunders Co., Philadelphia, PA, pp. 1029-1031 (2000).
WebMD.com, "Chemotherapy," page from website, http://my.webmd.com/content/article/45/1811_50450.htm?, printed Sep. 12, 2003.
Preliminary Amendment A of U.S. Appl. No. 11/124,654, filed May 6, 2005.

\* cited by examiner

MEDICAMENTS FOR CHEMOTHERAPEUTIC TREATMENT OF DISEASE

This application is a continuation-in-part of U.S. application Ser. No. 09/900,355 filed Jul. 6, 2001 now U.S. Pat. No. 7,648,695 which claims the benefit under 35 USC §119(e) of U.S. application 60/218,464 filed Jul. 14, 2000. The '355 application is also a continuation-in-part of U.S. application Ser. No. 09/130,041, filed on Aug. 6, 1998 now abandoned; U.S. application Ser. No. 09/635,276 filed on Aug. 9, 2000 now abandoned which is a continuation-in-part of U.S. application Ser. No. 09/216,787 filed Dec. 21, 1998 now U.S. Pat. No. 6,331,286; and U.S. application Ser. No. 09/799,785 filed on Mar. 6, 2001 now U.S. Pat. No. 7,390,668, which are herein incorporated by reference in their entirety.

BACKGROUND OF THE INVENTION

The present invention is related to certain chemotherapeutic medicaments and methods for treatment of human or animal tissue using chemotherapy.

Chemotherapy was developed to treat cancer and other disease with the promise of limiting the invasiveness of the therapeutic intervention. Ideally in the practice of chemotherapy, chemical agents that afford selective toxicity to diseased or otherwise undesirable tissue are administered to a patient. Frequently, these agents are administered systemically, with the expectation that the viability of certain tissues, such as the rapidly proliferating tissues of a cancerous tumor, will be selectively inhibited or destroyed. Unfortunately, most chemotherapeutic agents presently available offer limited specificity for such tissue, resulting in a high incidence of disagreeable side-effects, such as immune system suppression, nausea, and hair loss. While tremendous strides have been made in an effort to reduce or mitigate such side-effects, there still continues to be great difficulty in enhancement of specificity of the drug for tissues to be treated.

Therefore, it is an object of the present invention to provide new chemotherapeutic medicaments, new medical uses for such medicaments based on improved specificity of such medicaments for the desired target tissue to be treated, and methods for treatment using such medicaments, thereby resulting in improved treatment outcomes, increased efficacy and safety and reduced cost of treatment.

SUMMARY OF THE PRESENT INVENTION

The present invention is directed to new chemotherapeutic medicaments and certain medical uses of such medicaments, and methods for treatment using such medicaments, for treatment of human or animal tissue, wherein a primary active component of such medicaments is a halogenated xanthene or a halogenated xanthene derivative. In a preferred embodiment, the halogenated xanthene is Rose Bengal or a functional derivative of Rose Bengal. The halogenated xanthenes constitute a family of extremely useful agents that can be selectively delivered at high concentrations to certain tissues. Selective retention of such agents at high concentrations in the desired tissues results in decreased viability or death of such tissues (and hence provides a chemotherapeutic use of medicaments containing agents). Such medicaments are suitable for intracorporeal administration, and are thus intracorporeal chemotherapeutic medicaments. Such medicaments are also suitable for topical administration, and are thus topical chemotherapeutic medicaments. Such medicaments can also be called pharmaceutical compositions or agents.

Such chemotherapeutic medicaments are useful for the treatment of a variety of conditions affecting the skin and related organs, the mouth and digestive tract and related organs, the urinary and reproductive tracts and related organs, the respiratory tract and related organs, the circulatory system and related organs, the head and neck, the endocrine and lymphoreticular systems and related organs, various other tissues, such as connective tissues and various tissue surfaces exposed during surgery, as well as various tissues exhibiting microbial, viral, fungal or parasitic infection. These medicaments are available in various formulations that may include liquid, semisolid, solid or aerosol delivery vehicles, and are suitable for intracorporeal administration via various conventional modes and routes, including intravenous injection (i.v.), intraperitoneal injection (i.p.), intramuscular injection (i.m.), intracranial injection (i.c.), intratumoral injection (i.t.), intraepithelial injection (i.e.), transcutaneous delivery (t.c.), and per oesophageal (p.o.) administration. Additionally, such medicaments are suitable for topical administration via various conventional modes and routes, including topical application directly to or proximal to certain tissues. The active ingredients in such chemotherapeutic medicaments produce a desirable therapeutic response, such as destruction of microbial infection, reduction or elimination of tissue irritation, reduction or elimination of hyperproliferative tissue, reduction or elimination of cancerous or precancerous tissue, reduction or elimination of surface or subsurface lipocytes or lipid deposits, and many other similar indications.

In a preferred embodiment, such chemotherapeutic medicaments are used for treatment of a variety of conditions affecting the skin and related organs.

In another preferred embodiment, such chemotherapeutic medicaments are used for treatment of a variety of conditions affecting the mouth and digestive tract and related organs.

In another preferred embodiment, such chemotherapeutic medicaments are used for treatment of a variety of conditions affecting the urinary and reproductive tracts and related organs.

In another preferred embodiment, such chemotherapeutic medicaments are used for treatment of a variety of conditions affecting the respiratory system and related organs.

In another preferred embodiment, such chemotherapeutic medicaments are used for treatment of a variety of conditions affecting the circulatory system and related organs.

In another preferred embodiment, such chemotherapeutic medicaments are used for treatment of a variety of conditions affecting the head and neck.

In another preferred embodiment, such chemotherapeutic medicaments are used for treatment of a variety of conditions affecting the endocrine and lymphoreticular systems and related organs.

In another preferred embodiment, such chemotherapeutic medicaments are used for treatment of a variety of conditions affecting various other tissues, such as connective tissues and various tissue surfaces exposed during surgery.

In another preferred embodiment, such chemotherapeutic medicaments are used for treatment of a variety of conditions related to microbial or parasitic infection.

In another preferred embodiment, such chemotherapeutic medicaments are produced in various formulations including liquid, semisolid, solid or aerosol delivery vehicles, as well as in tablet, capsule, suppository, and other similar forms.

In a preferred embodiment, the present invention is directed to a medicament adapted for intracorporeal injection, the medicament consisting of: a hydrophilic vehicle containing a halogenated xanthene, wherein said halogenated xanthene is a compound selected from the group consisting of Erythrosin B, Phloxine B, Rose Bengal, and 4,5,6,7-Tetrabromoerythrosin, said halogenated xanthene at a concentration of from greater than approximately 0.1% to less than approximately 20%, and an electrolyte selected from the group consisting of sodium, potassium, calcium and magnesium chlorides, phosphates, and nitrates, wherein the electrolyte is at a concentration of approximately 0.1-2%, or wherein the electrolyte is at a level sufficient to provide an osmolality of the medicament of greater than approximately 100 mOsm/kg, said medicament having a pH in the range from approximately 4 to 10, and wherein: said medicament is sterile; said medicament contains pyrogenic material at a level of no more than 10 Endotoxin Units per mL; and said medicament contains particulate material at a level of no more than 300 particles of size 25 microns or larger and no more than 3000 particles of size 10 microns or larger.

BRIEF DESCRIPTION OF THE DRAWINGS

In describing the preferred embodiments, reference is made to the accompanying drawings wherein.

DETAILED DESCRIPTION OF THE PRESENTLY PREFERRED EMBODIMENTS

Figure 1A:
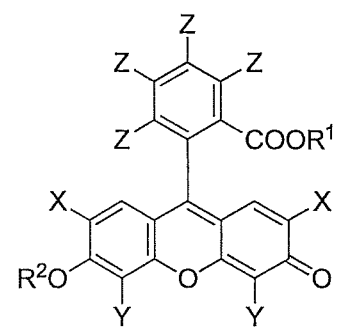
FIG. 1(a) shows the generalized chemical structure of the halogenated xanthenes.

The present invention is directed to new chemotherapeutic medicaments and certain medical uses of such chemotherapeutic medicaments, and methods for chemotherapeutic treatment using such medicaments, for treatment of human or animal tissue, wherein a primary active component of such medicaments is a halogenated xanthene or halogenated xanthene derivative. The inventors of the present invention have discovered that such halogenated xanthenes, as discussed in more detail infra, exhibit desirable chemotherapeutic effects when applied to or otherwise delivered to certain human or animal tissues. The desirable effects include reduction or elimination of disease or diseased tissue or other undesirable conditions, including eradication of cancerous or pre-cancerous tumors and infectious agents. The treatment is applicable to a variety of conditions affecting the skin and related organs, the mouth and digestive tract and related organs, the urinary and reproductive tracts and related organs, the respiratory tract and related organs, the circulatory system and related organs, the head and neck, the endocrine and lymphoreticular systems and related organs, various other tissues, such as tissues exposed during surgery, as well as various tissues exhibiting microbial, viral, fungal or parasitic infection.

In a preferred embodiment, such medicaments are produced in various formulations suitable for intracorporeal or topical administration, including in various liquid, semisolid, solid or aerosol delivery vehicles, as well as in tablet, capsule, suppository, and other similar forms. Such medicament formulations are suitable for delivery via various conventional modes and routes (hereafter defined as administration), including intravenous injection (i.v.), intraperitoneal injection (i.p.), intramuscular injection (i.m.), intracranial injection (i.c.), intratumoral injection (i.t.), intraepithelial injection (i.e.), transcutaneous delivery (t.c.), per oesophageal (p.o.) administration, and topical application; additional administrative modes and routes include intraabdominal, intraapendicular, intraarterial, intraarticular, intrabronchial, intrabuccal, intracapsular (such as for example capsule in knee, elbow and eye), intracardial, intracartilaginous, intracavitary, intracephalic, intracolic, intracutaneous, intracystic, intradennal, intraductal, intraduodenal, intrafascicular, intrafat, intrafilar, intrafissural, intragastric, intraglandular, intrahepatic, intraintestinal, intralamellar, intralesional, intraligamentous, intralingual, intramammary, intramedullary, intrameningeal, intramyocardial, intranasal, intraocular, intraoperative, intraoral, intraosseous, intraovarian, intrapancreatic, intraparietal, intrapelvic, intrapericardial, intraperineal, intraperitoneal, intraplacental, intrapleural, intrapontine, intraprostatic, intrapulmonary, intrarachidian, intrarectal, intrarenal, intrascleral, intrascrotal, intrasegmental, intrasellar, intraspinal, intrasplenic, intrasternal, intrastromal, intrasynovial, intratarsal, intratesticular, intrathoracic, intratonsillar, intratracheal, intratubal, intratympanic, intraureteral, intraurethral, intrauterine, intravaginal, intravascular, intraventricular, intravertebral, intravesical, or intravitreous administration. The inventors have found that direct injection into diseased tissue (i.e., intralesional injection) is a particularly favored means of administration for treatment of focal disease, such as many forms of cancer, since it concentrates and maximizes the therapeutic effects of the medicaments in target tissue while minimizing potential for deleterious effect elsewhere in the patient.

1. Properties of the preferred active components and medicament formulations.

The inventors of the present invention have discovered a class of agents that are broadly applicable for producing chemotherapeutic medicaments for treatment of disease in certain human and animal tissues. These agents are referred to as halogenated xanthenes and are illustrated in FIG. 1a, where the symbols X, Y, and Z represent various elements present at the designated positions, and the symbols $R^1$ and $R^2$ represent various functionalities present at the designated positions.

Selected properties (such as chemical constituents at positions X, Y, and Z and functionalities $R^1$ and $R^2$) of representative halogenated xanthenes are summarized in attached Table 1. Certain general properties of this class of agent are discussed in further detail in U.S. Ser. No. 09/130,041 filed on Aug. 6, 1998, U.S. Ser. No. 09/184,388 filed on Nov. 2, 1998, U.S. Ser. No. 09/216,787 filed on Dec. 21, 1998, U.S. Ser. No 09/635,276 filed on Aug. 9, 2000, U.S. Ser . No. 09/799,785 filed on Mar. 6, 2001, and U.S. Ser. No. 09/817,448 filed on Mar. 26, 2001, which are herein incorporated by reference in their entirety. In general, the halogenated xanthenes are characterized by a low cytotoxicity (toxicity to cells) at low concentration, a propensity for selective concentration or retention in certain tissues and cells, a high cytotoxicity upon such concentration or retention, and by chemical and physical properties that are substantially unaffected by the local chemical environment or by the attachment of functional derivatives at positions $R^1$ and $R^2$. Such factors make these chemical agents, and in particular chemotherapeutic medicaments formulated from such agents, excellent for the treatment of disease in human and animal tissues.

It is thus one preferred embodiment of the present invention that a chemotherapeutic medicament be produced that contains, as an active ingredient at a concentration of from greater than approximately 0.001% to less than approximately 20%, at least one halogenated xanthene. Further, the inventors have found that halogenated xanthene concentrations above approximately 0.1% to 3% are particularly useful for chemotherapeutic use, since lower concentrations are generally insufficient to elicit necrosis or other desired mechanisms of death in target tissues. Thus, in a further preferred embodiment, the concentration of the at least one halogenated xanthene is in the range of from approximately 1% to 20%, and more preferably from approximately 3% to 20%. In still a further preferred embodiment, the concentration of the at least one halogenated xanthene is approximately 10%, as such concentrations are sufficient to effect chemotherapeutic response and are readily formulated and have proven, in the experience of the inventors, to be highly stable and readily handled both in manufacture and use. These preferred concentrations may be weight to volume (w/v) or weight to weight (w/w).

Figure 1B:
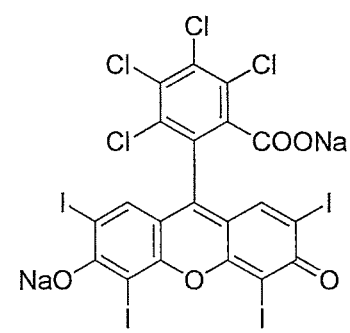
FIG. 1(b) shows the chemical structure of Rose Bengal.

It is preferred that this medicament include the halogenated xanthene Rose Bengal (4,5,6,7-Tetrachloro-2',4',5',7'-tetraiodofluorescein, illustrated in FIG. 1b), and more preferably the disodium form of Rose Bengal (i.e., disodium Rose Bengal) which is stable under physiologic conditions.

Examples of other halogenated xanthenes which can be used in the medicaments of the present invention include one or more of the following Fluorescein derivatives: 4',5'-Dichlorofluorescein; 2',7'-Dichlorofluorescein; 4,5,6,7-Tetrachlorofluorescein; 2',4',5',7'-Tetrachlorofluorescein; Dibromofluorescein; Solvent Red 72; Diiodofluorescein; Eosin B; Eosin Y; Ethyl Eosin; Erythrosin B; Phloxine B; Rose Bengal; 4,5,6,7-Tetrabromoerythrosin; Mono-, Di-, or Tribromoerythrosin; Mono-, Di-, or Trichloroerythrosin; Mono-, Di-, or Trifluoroerythrosin; 2',7'-Dichloro-4,5,6,7-Tetrafluorofluorescein; 2',4,5,6,7,7'-Hexafluorofluorescein; 4,5,6,7-Tetrafluorofluorescein, 2',4',5,5',6,7'-Hexaiodofluorescein; 2',4',5,5',7,7'-Hexaiodofluorescein; 2',4',5',6,7,7'-Hexaiodofluorescein; 2',4',5,5',6,7,7'-Heptaiodofluorescein; 4-Chloro-2',4',5,5',6,7'-hexaiodofluorescein; 4-Chloro-2',4',5,5',7,7'-hexaiodofluorescein; 4-Chloro-2',4',5',6,7,7'-hexaiodofluorescein; 4-Chloro-2',4',5,5',6,7,7'-heptaiodofluorescein; 4,5-Dichloro-2',4',5',6,7,7'-hexaiodofluorescein; 4,6-Dichloro-2',4',5,5',7,7'-hexaiodofluorescein; and 4,7-Dichloro-2',4',5,5',6,7'-hexaiodofluorescein.

As an example of these desirable chemical, biochemical, and physical properties, the inventors have found that the prototypical halogenated xanthene, Rose Bengal, will accumulate preferentially in (e.g., target) some tumors and other tissues and pathogenic entities and exhibit high cytotoxicity within such tumors, tissues and pathogenic entities, while exhibiting negligible systemic cytotoxicity or local cytotoxicity in surrounding healthy tissues. Such agents also possess the ability to clear rapidly from healthy tissue in the body. Furthermore, such agents have a relatively low cost.

For example, to a first approximation, an agent's potential for tissue accumulation can be estimated based on the partition coefficient, $K_p$. This in vitro parameter is purported to have predictive value relating to in vivo agent delivery at the cellular level. In particular, a value greater than unity is considered to indicate agents capable of localizing in tumor or other diseased tissue, and thereby being capable of exhibiting enhanced chemotherapeutic efficacy in such tissue. $K_p$ is determined by measuring the ratio of equilibrium concentrations of an agent in a lipophilic phase (n-octanol) contacted with an aqueous phase (phosphate buffered saline, PBS, pH=7.4). Comparative values of $K_p$ are shown in Table 2. The large $K_p$ values for the halogenated xanthenes suggest that the halogenated xanthenes will exhibit a preference for concentration or accumulation in tumor or other diseased tissue, and should thereby be capable of exhibiting superior chemotherapeutic efficacy in such tissue. However, as explained below, the inventors have discovered that halogenated xanthenes exhibit a much greater chemotherapeutic efficacy in such tissue than could be predicted solely from the $K_p$ values shown in Table 2.

Figure 2:
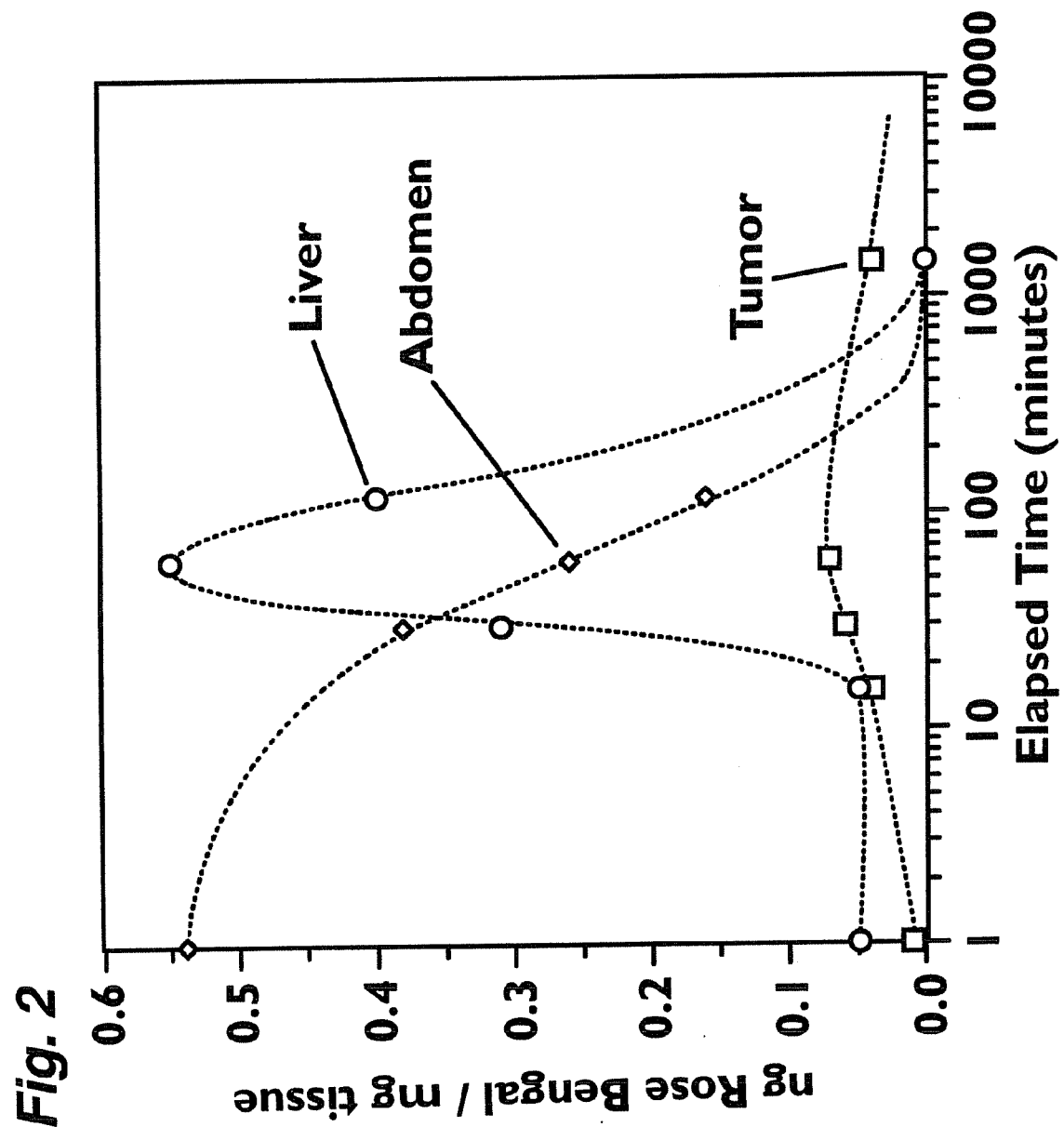
FIG. 2 shows example pharmacokinetic behavior of Rose Bengal upon intraperitoneal injection into nude mice with an implanted MCF-7 human breast cancer tumor.

The following examples illustrate this preference for accumulation in tumor tissue by the halogenated xanthenes:

Tumor cell suspensions (e.g., melanoma, breast tumor, liver tumor, renal carcinoma, gal bladder tumor or prostate tumor) were injected subcutaneously into the flanks of nude mice and resulted in the formation of primary tumors, within a few weeks, at the injection site having a volume of approximately 0.25 cm$^3$. A solution of Rose Bengal (50-100 μL of 0.5% Rose Bengal in saline) was then administered by intraperitoneal injection (i.p.) to the tumor-bearing mice, and the injected mice sacrificed at timed intervals following injection. Tissue samples (liver, abdominal wall, and tumor) were immediately obtained from the sacrificed mice, homogenized, centrifuged for 10 minutes at 1520×g, and the resulting supernatant collected and analyzed fluorimetrically. This allowed the pharmacokinetics of the administered Rose Bengal to be easily observed, as illustrated in FIG. 2. The data in FIG. 2 show that Rose Bengal rapidly diffuses from normal tissue (e.g., abdominal wall) and is efficiently entrapped and excreted through the liver, with concentrations in these tissues diminishing to unmeasurable levels within 24 hours. At the same time, persistent accumulation occurs in tumor tissue, with greater than 50% of maximum measured agent concentration maintained in such tissues for periods in excess of 24 hours.

If such implanted tumors are directly injected with Rose Bengal, similar selective, persistent accumulation occurs.

For example, BNL/SV40 liver cell tumor cells injected into the flanks of nude mice, as described supra, resulted in the formation of primary tumors, within a few weeks, at the injection site and have a volume of approximately 0.25 cm$^3$. Intratumoral (i.t.) and peritumoral p.t.) injection of a 10% solution of Rose Bengal (50 μL of 10% Rose Bengal in saline) resulted in marked red staining of the tumor and the surrounding flank. Within 7 days this Rose Bengal cleared from normal tissue, but the tumor tissue remained stained. Over a period of several weeks the previously rapidly growing tumor exhibited stasis, with no significant change in tumor volume and a marked absence of mitotic figures (e.g., exhibiting only non-hyperproliferative cells).

Further, peritumoral injection alone (e.g., injection into normal tissue around the outside margins of the tumor) of the above Rose Bengal exhibited no detectable retention in normal tissue after 24 hours. Notably, no significant effect on normal tissue, nor on the adjacent tumor tissue, was noted upon peritumoral injection alone.

Hence, the administered Rose Bengal in these examples not only exhibited selective, persistent accumulation in tumor tissue, but this accumulated agent also exhibits chemotherapeutic efficacy with minimal or no measurable side effects in healthy tissue.

This chemotherapeutic effect for Rose Bengal is further illustrated by the following example. An adult, female dog with a naturally-occurring, recurrent aggressive sarcoma tumor (approximately 20 cc in volume) was treated by injection of approximately 5 cc of a 10% solution of Rose Bengal at several locations throughout the tumor volume. After a period of five days, a follow-up examination of the animal indicated a measurable decrease in tumor density along with significant edema and apparent necrosis of large sections of the tumor. Another follow-up examination after 19 days indicated a further measurable decrease in tumor size. Such a response is indicative of chemotherapeutic activity of the injected Rose Bengal within the tumor mass. It is also notable that no significant side-effects were noted in the healthy tissue surrounding the tumor.

In contrast, i.t. administration of a different class of agent, indocyanine green ($K_p=99$), into various murine tumors showed that within 24 hours this agent substantively migrates out of tumors, with residual agent tending to accumulate in peritumoral tissues. Moreover, no chemotherapeutic effect was evidenced upon such administration of such agent. Hence, while the $K_p$ value for indocyanine green is nearly ten-fold larger than that of Rose Bengal (and as such, indocyanine green is, by the conventional model based solely on $K_p$, expected to accumulate strongly in tumor tissue), the tissue localization properties of the two agents are clearly completely different. Furthermore, even at the relatively high concentrations in the immediate vicinity of the injection site, indocyanine green was found to exhibit no chemotherapeutic activity.

Thus, the halogenated xanthenes, and in particular Rose Bengal, exhibit an unexpectedly marked preference for selective accumulation and retention in tumor and other diseased tissue upon administration, and that once present in such tissue, said halogenated xanthenes can be utilized as potent, highly tissue- or disease-specific chemotherapeutic agents.

The toxicology data shown in Table 2 indicate that the halogenated xanthenes are relatively non-toxic, and yet, in contrast to agents such as indocyanine green, they exhibit unanticipated chemotherapeutic properties. One possible explanation for this may be that such chemotherapeutic properties of the halogenated xanthenes, and in particular of Rose Bengal, are the result of their special combination of modest intrinsic cytotoxicity and marked propensity for persistent, selective accumulation in certain cells, such as cancerous cells: based, for example, on simple first-order kinetics, such modestly cytotoxic agents, upon becoming present in cells at high local concentrations for extended periods of time, should exhibit chemotherapeutic properties.

Figure 3:
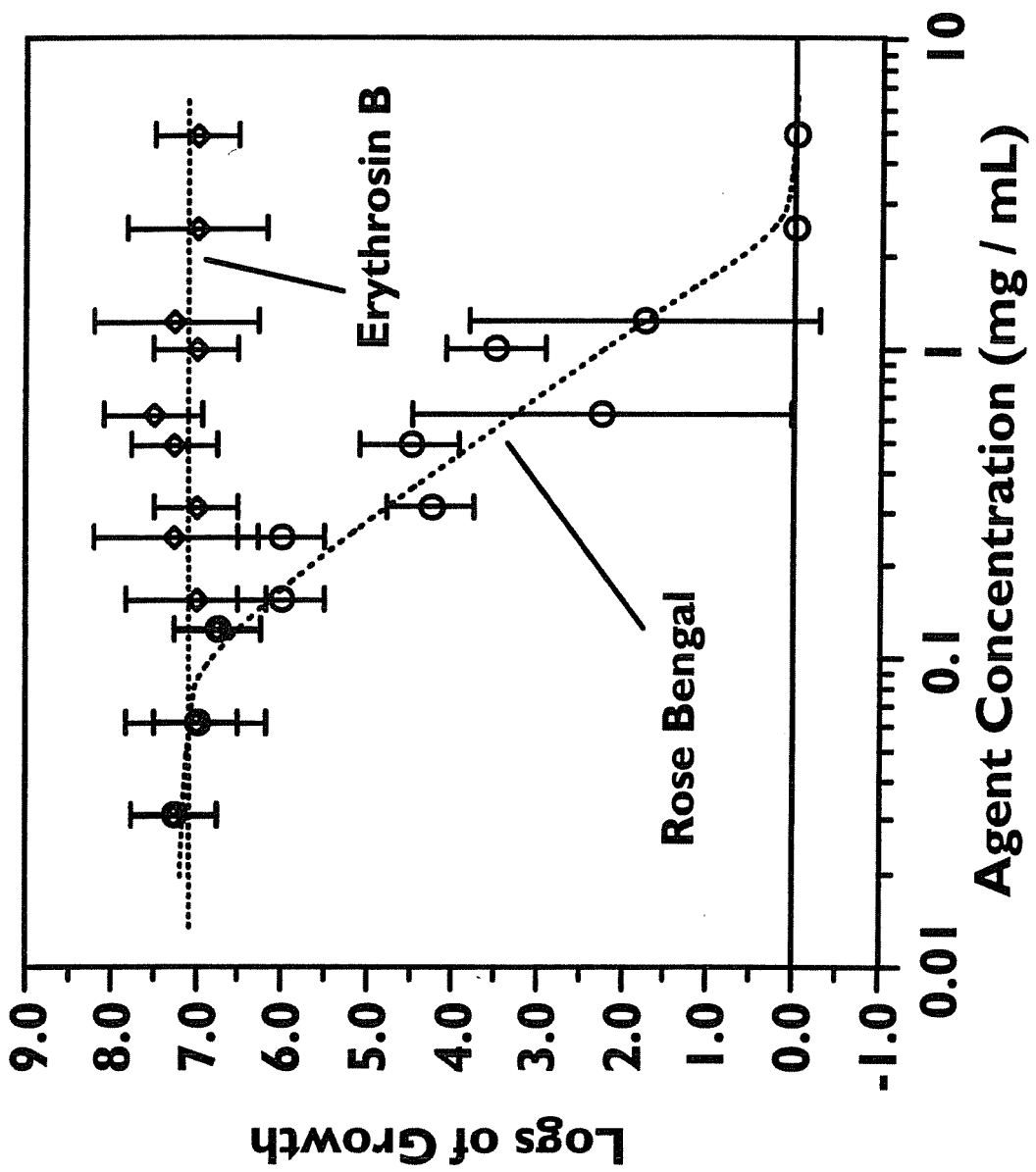
FIG. 3 illustrates cytotoxic effects in bacteria upon exposure to either Rose Bengal or Erythrosin B as a function of agent concentration.
Figure 4:
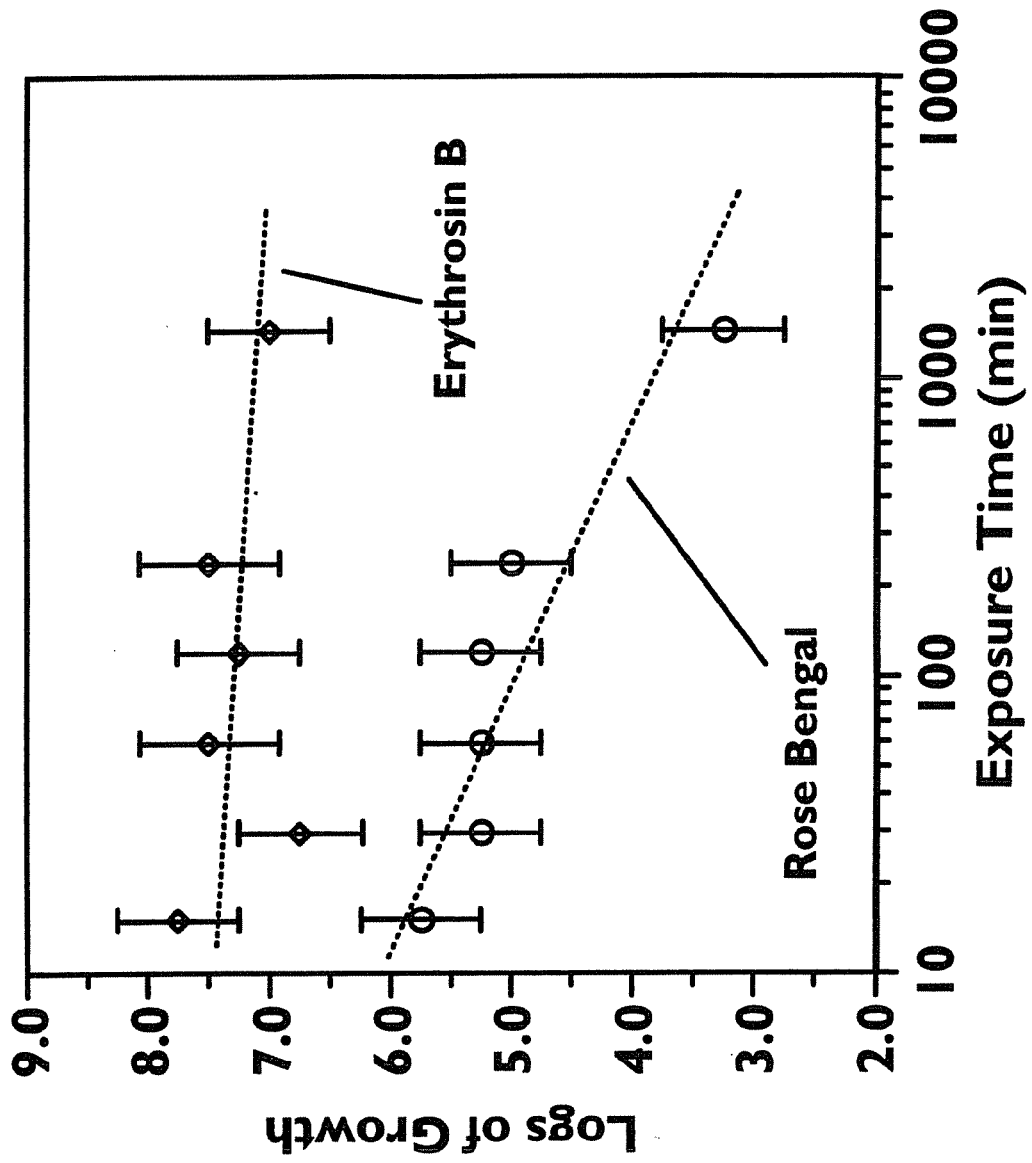
FIG. 4 illustrates the cytotoxic effects of exposure to either Rose Bengal or Erythrosin B as a function of exposure duration.

The inventors tested this hypothesis by evaluating the chemotherapeutic properties of Rose Bengal and Erythrosin B on cultures of the bacterium *Staphylococcus aureus*. These data are illustrated in FIGS. 3 and 4. In both illustrations, test cultures were exposed to the indicated agents at the indicated concentrations for the indicated times; cytotoxicity was subsequently estimated by serial dilution (10×dilution per step) of the treated cell cultures into 96-well plates containing fresh culture media; these samples were then incubated under standard conditions. Viability (e.g., Logs of Growth) for each test culture was then estimated by counting the number of dilution steps resulting in positive cell growth. Cytotoxicity upon exposure to a particular agent is thereby estimated by the reduction in viability relative to unexposed (e.g., control) cultures. FIG. 3 illustrates the cytotoxic effects of a 90 minute exposure of *S. aureus* to either Rose Bengal or Erythrosin B. In this figure, Rose Bengal exhibits a marked chemotherapeutic response that is concentration dependent, while Erythrosin B exhibits no significant chemotherapeutic response for this brief exposure duration over the range of concentrations tested. FIG. 4 illustrates the cytotoxic effects on *S. aureus* for various durations of exposure to Rose Bengal or Erythrosin B (each administered at a concentration of 0.5 mg/mL). These data show that the chemotherapeutic properties of the halogenated xanthenes are dependent on exposure time. Notably, the negative slopes for the trend lines of both agents are indicative of cumulative cytotoxicity that is time dependent. The shallower slope for Erythrosin B indicates lower cytotoxicity in this model (e.g. *S. aureus*), consistent with the results illustrated in FIG. 3. Hence, certain agents that exhibit a modest, but nonetheless finite, cytotoxicity (such as for example, but not limited to, the halogenated xanthenes) should afford chemotherapeutic modality when administered to certain tissues, wherein such administration results in sufficient local concentration of such agents for a sufficient period so as to cause local cytotoxic effects (e.g., chemotherapy) in such tissues.

In addition to superior suitability for direct administration into desired targeted tissue to be treated, such as a focal tumor, the preference of the halogenated xanthenes for accumulation in certain types of tissues provides a basis for highly-selective, systemic delivery of the halogenated xanthenes to such tissues. For example, Rose Bengal's relatively large partition coefficient is indicative of a preference for accumulation in lipophilic tissue, such as cutaneous lipocytes. Systemic administration of Rose Bengal, for example as an aqueous solution administered via intraperitoneal injection (i.p.) or per oesophagus (p.o.) administration, resulted in highly selective accumulation of said agent in certain tissues, such as in the cutaneous fat deposits of obese laboratory mice. Histologic examination of skin samples from such animals showed that the accumulated agent was substantively limited to cutaneous lipocytes.

Moreover, the facility with which the halogenated xanthenes target specific tissues or other sites can be further optimized by attachment of specific functional derivatives at positions $R^1$ and $R^2$, so as to change the chemical partitioning and/or biological activity of the agent. For example, attachment of one targeting moiety or more at positions $R^1$ or $R^2$ can be used to improve targeting to specific tissues, such as cancerous tumor tissues or sites of localized infection. An example of this is esterification at position $R^1$ with a short aliphatic alcohol, such as n-hexanol, to produce a derivatized agent exhibiting enhanced partitioning into lipid-rich tumor tissues.

It is thus a further preferred embodiment that at least one of the at least one halogenated xanthene active ingredients includes at least one targeting moiety selected from a group that includes deoxyribonucleic acid (DNA), ribonucleic acid (RNA), amino acids, proteins, antibodies, ligands, haptens, carbohydrate receptors or complexing agents, lipid receptors or complexing agents, protein receptors or complexing agents, chelators, encapsulating vehicles, short- or long-chain aliphatic or aromatic hydrocarbons, including those containing aldehydes, ketones, alcohols, esters, amides, amines, nitriles, azides, or other hydrophilic or hydrophobic moieties. A further example of this embodiment is derivatization of Rose Bengal with a lipid (at position $R^1$, via esterification), so as to increase the lipophilicity of Rose Bengal, and thereby modify its targeting properties in a patient. An additional further example of this embodiment is derivatization of Rose Bengal with folate (at position $R^1$, via esterification or other modes of attachment), so as to increase selective targeting of cancer and other cells exhibiting enhanced folate receptor activity or folate metabolism.

As an alternative to use of the aforementioned targeting moieties, in a further embodiment, $R^1$ and $R^2$ may be independently selected from hydrogen ($H^+$), sodium ($Na^+$), potassium ($K^+$), calcium ($Ca^+$) and ammonium ($NH_4^+$) ions. The inventors have found that such analogs (such as sodium or disodium Rose Bengal) can be preferable due to their intrinsic stability under physiologic conditions and the inherent avoidance of components that might themselves be physiologically active.

As a further example of the desirable chemical, biochemical, and physical properties of the halogenated xanthenes and halogenated xanthene derivatives, the inventors of the present invention have shown that these agents are readily cleared from healthy tissues in a matter of several hours, and are rapidly excreted in bile, urine and feces, without doing damage to healthy tissue while in the body. Further examples of the desirable properties of the halogenated xanthenes and halogenated xanthene derivatives are that the halogenated xanthenes and halogenated xanthene derivatives are easily synthesized using simple, low-cost synthetic methods, can be readily purified, and exhibit excellent stability (such as a long shelf life without need for refrigeration or storage under an inert atmosphere).

Because the halogenated xanthenes and their derivatives are, in general, fine solid powders in their pure form, it is preferred that, for proper delivery to desired tissues, such agents be formulated in appropriate delivery vehicles. Specifically, such formulations are preferred so as to facilitate agent delivery into the body and subsequent contact with, and delivery to, desired tissues to be treated. Approaches to such formulation will be generally known to those of ordinary skill in the art.

It is thus a further preferred embodiment of the present invention that at least one halogenated xanthene or halogenated xanthene derivative be formulated as a medicament in a form suitable for intracorporeal or topical administration via various conventional modes and routes. Such suitable forms include, for example, medicaments formulated in a liquid, semisolid, solid or aerosol delivery vehicle, including in vehicles of the following natures: aqueous, non-aqueous or particulate suspensions, solutions, creams, ointments, gels, syrups, micro-droplet sprays, suppositories, tablets and capsules. The at least one halogenated xanthene or halogenated xanthene derivative may be dissolved or suspended in such delivery vehicle, wherein this vehicle may, in addition to the at least one halogenated xanthene or halogenated xanthene derivative, include various builders, stabilizers, emulsifiers or dispersants, preservatives, buffers, electrolytes, and tissue penetrating or softening agents. Such components of the delivery vehicle may be present as the primary component (by weight or volume) of the medicament, or as a minor component that serves in an adjuvant role in agent delivery with no adverse affect on tissue or treatment outcome.

Examples of appropriate builders include cellulose and cellulose derivatives, such as starch, and alginates. Additional examples include various carboxymethylcelluloses and derivatives thereof, especially those of medium to high viscosity, such as USP carboxymethylcellulose.

Examples of appropriate stabilizers, emulsifiers or dispersants include liposomes, nanoparticulates and nanodispersions, microparticulates and microdispersions, as well as various lipids, detergents and other surfactants.

Examples of appropriate preservatives include benzalkonium chloride, thimerosal, quaternary amines and urea. Additional examples of appropriate preservatives include chlorhexidine, imidurea, methyl-paraben and propyl-paraben. The inventors have found that it is generally preferable to avoid use of preservatives, many of which may deleteriously interfere with the medicament or formulation thereof, or may complex with or otherwise interact with or interfere with delivery of the active halogenated xanthene component therein. To the extent that a preservative is to be used, the inventors have found that imidurea is preferred as it does not appear to interact with the halogenated xanthenes, either in the medicament or upon administration, nor to deleteriously affect the medicament formulation.

Examples of appropriate buffers include monobasic or dibasic phosphate salts, citrate salts, bicarbonate salts, and ethanolamine.

Examples of appropriate electrolytes include sodium, potassium, calcium and magnesium chlorides, phosphates, and nitrates. Sodium, such as in the form of sodium chloride, is a preferred embodiment as the electrolyte due to its inherent physiologic compatibility. The inventors have found that it is preferable that such electrolyte be present in the medicament at a concentration of approximately 0.1-2%, and more preferably at a concentration of approximately 0.5-1.5%, and even more preferably at a concentration of approximately 0.8-1.2%, and most preferably at a concentration of approximately 0.9%. Electrolytes at such levels increase the osmolality of the medicament, which the inventors have found to increase the preference for partitioning of the halogenated xanthene component into tissue. Thus, as an alternative to the previously specified range of electrolyte concentrations, osmolality may be used to characterize, in part, the electrolyte level of the preferred medicament. It is preferred that the osmolality of the medicament be greater than approximately 100 mOsm/kg, and more preferably that it be greater than approximately 250 mOsm/kg, and most preferably that it be approximately 300-500 mOsm/kg.

Examples of appropriate tissue penetrating, softening or solvating agents and adjuvants include:

various sulfoxides, such as DMSO and decylmethylsulfoxide;

various aliphatic and fatty alcohols, such as ethanol, propanol, hexanol, octanol, benzyl alcohol, decyl alcohol, lauryl alcohol, and stearyl alcohol;

various linear and branched, saturated and unsaturated fatty acids, such as lauric acid, caproic acid, capric acid, myristic acid, stearic acid, oleic acid, isovaleric acid, neopentanoic acid, trimethyl hexanoic acid, neodecanoic acid and isostearic acid;

various aliphatic and alkyl fatty acid esters, such as isopropyl n-butyrate, isopropyl n-hexanoate, isopropyl n-decanoate, isopropyl myristate, isopropyl palmitate, octyldodecyl myristate, ethyl acetate, butyl acetate, methyl acetate, methylvalerate, methylpropionate, diethyl sebacate and ethyl oleate;

various polyols, such as propylene glycol, polyethylene glycol, ethylene glycol, diethylene glycol, triethylene glycol, diproplyene glycol, glycerol, propanediol, butanediol, pentanediol and hexanetriol;

various amides, such as urea, dimethylacetamide, diethyltoluamide, dimethylformamide, dimethyloctamide, dimethyldecamide; biodegradable cyclic urea, such as 1-alkyl-4-imidazolin-2-one; pyrrolidone derivatives, such as 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-methyl-4-methyoxycarbonyl-2-pyrrolidone, 1-methyl-4-methyoxycarbonyl-2-pyrrolidone, 1-lauryl-4-methyoxycarbonyl-2-pyrrolidone, N-cyclohexylpyrrolidone, N-dimethylaminopropylpyrrolidone, N-cocoalkypyrrolidone, N-tallowalkylpyrrolidone; biodegradable pyrrolidone derivatives, such as fatty acid esters of N-(2-hyroxyethyl)-2-pyrrolidone; cyclic amides, such as 1-dodecylazacycloheptane-2-one (Azone®), 1-geranylazacycloheptan-2-one, 1-farnesylazacycloheptan-2-one, 1-geranylgeranylazacycloheptan-2-one, 1-(3,7-dimethyloctyl)azacycloheptan-2-one, 1-(3,7,11-trimethydodecyl)azacycloheptan-2-one, 1-geranylazacyclohexane-2-one, 1-geranylazacyclopentan-2,5-dione, 1-farnesylazacyclopentan-2-one; hexamethylenelauramide and its derivatives; and diethanolamine and triethanolamine;

various surfactants, such as anionic surfactants, including sodium laurate and sodium lauryl sulfate; cationic surfactants, including cetyltrimethyl ammonium bromide, tetradecyltrimethylammonium bromide, benzalkonium chloride, octadecyltrimethylammonium chloride, cetylpyridinium chloride, dodecyltrimethylammonium chloride, hexadecyltrimethylammonium chloride; non-ionic surfactants, such as Polaxamer (231, 182, 184), Brij (30, 93, 96, 99), Span (20,40,60,80,85), Tween (20, 40,60,80), Myrj (45,51,52), Miglyol 840; various bile salts, such as sodium cholate, sodium salts of taurocholic, glycholic, desoxycholic acids; lecithin;

various terpenes, including hydrocarbons, such as D-limonene, α-pinene, β-carene; various terpene alcohols, including α-Terpineol, terpinen-4-ol, carvol; various terpene ketones, including carvone, pulegone, piperitone, menthone; various terpene oxides, including cyclohexane oxide, limonene oxide, α-pinene oxide, cyclopentene oxide, 1,8-cineole; various terpene oils, including ylang ylang, anise, chenopodium, eucalyptus;

various alkanones, such as N-heptane, N-octane, N-nonane, N-decane, N-undecane, N-dodecane, N-tridecane, N-tetradecane, N-hexadecane;

various organic acids, such as salicylic acid and salicylites (including their methyl, ethyl, and propyl glycol derivatives), citric and succinic acid.

The inventors have found that therapeutic delivery of the halogenated xanthene component of these medicaments is most favorable when the medicament has a pH close to physiologic pH (i.e., approximately 7), and especially when the pH is greater than about 4, thereby assuring that the halogenated xanthenes remain in dibasic form in the medicament. Thus, in a preferred embodiment, it is preferred that the pH of the medicament be in the range from approximately 4-10, and more preferably in the range from approximately 5-9, and most preferably in the range from approximately 6-8.

Since the medicament is often intended for intracorporeal delivery (such as by injection) it is further preferred that the medicament be sterile, such as required for conformance to U.S. Pharmacopeia (USP) test <71>, and further that it contain negligible levels of pyrogenic material, such that it conforms to USP <85> (limulus amebocyte lysate assay) or to USP <151> (rabbit pyrogen test), or to substantially equivalent requirements, at a pyrogen level equivalent to not more than (NMT) 10 endotoxin units (EU) per mL. Moreover, the medicament should also conform to requirements limiting content of particulate matter as defined in USP <788> (i.e., NMT 3000particulates greater than 10 microns in size, and NMT 300 particulates greater than 25 microns in size, per container) or substantially equivalent requirements. Each of these documents is attached and incorporated herein by reference.

Finally, the inventors have found that a hydrophilic vehicle is preferred for the medicament to maximize preference for partitioning of the halogenated xanthene component into tissue. Accordingly, it is preferred that the vehicle contain a minimum of non-hydrophilic components that might interfere with such partitioning. It is most preferred that this vehicle consist substantially of water.

Accordingly, the inventors have found that a preferred formulation of the medicaments contain, in a hydrophilic vehicle:

(1) at least one active halogenated xanthene ingredient at a concentration of from greater than approximately 0.1% to less than approximately 20%, and more preferably at a concentration in the range of from approximately 3% to 20%, and most preferably that this concentration is approximately 10%; and (2) an electrolyte selected from sodium, potassium, calcium and magnesium chlorides, phosphates, and nitrates, and more preferably sodium chloride, wherein the electrolyte is present at a concentration of approximately 0.1-2%, and more preferably at a concentration of approximately 0.5-1.5%, and even more preferably at a concentration of approximately 0.8-1.2%, and most preferably at a concentration of approximately 0.9%, or alternately at a level sufficient to provide an osmolality of greater than approximately 100 mOsm/kg, and more preferably greater than 250mOsm/kg, and most preferably approximately 300-500 mOsm/kg.

In a further preferred embodiment, the hydrophilic vehicle consists of water, and more preferably, the medicament contains only one halogenated xanthene ingredient.

In a further preferred embodiment, the medicament has a pH close to physiologic pH (i.e., approximately 7), and especially a pH of greater than about 4, and preferably in the range from approximately 5-10, and most preferably in the range from approximately 6-8.

In another preferred embodiment, the at least one halogenated xanthene consists of Rose Bengal or a functional derivative of Rose Bengal, including those containing any combination of hydrogen ($H^+$), sodium ($Na^+$), potassium ($K^+$), calcium ($Ca^+$) or ammonium ($NH_4^+$) ions at both positions $R^1$ and $R^2$.

It is most preferred that the medicament contain only, in a hydrophilic vehicle, at least one halogenated xanthene and an electrolyte, wherein such medicament has a pH close to physiologic pH. An example of such a preferred medicament is an aqueous solution consisting of disodium rose bengal in 0.9% saline having a pH of 5 to 10, and more preferably a pH of approximately 7.

The inventors have found that the aforementioned medicaments are particularly suitable for treatment of focal disease, such as benign, cancerous or precancerous tumors or other lesions, upon intralesional injection, particularly where the medicament is injected into target tissue, such as a cancerous lesion, at a level (i.e., medicament volume) of between approximately 0.1 and 2relative to the volume of the lesion, and more preferably at a level of between approximately 0.5 and 1 times the volume of the lesion, so as to uniformly infiltrate the injected tissue. The inventors have further found that such injection is optimally effected using a fine gauge needle for injection, preferably 22-24 gauge or smaller, and more preferably 26 gauge or smaller, to minimize leakage of injected medicament via the needle track. It is further preferred that such injection be performed using a minimum of punctures into the injected tissue, whereby the needle be inserted into the injected tissue a minimum number of times and then, using a "fanning" or similar technique, starting at the margin and slowly withdrawing the needle during each fractionated injection. Multiple injection tracks may thereby be applied, using a single puncture when possible and while re-injecting at multiple angles into the treated lesion while minimizing tearing and leakage until the entire tissue volume is uniformly infiltrated. Alternately, an injection device having several tips adapted for simultaneous injection or infusion to multiple locations within the target tissue, such as that described by Edwards et al. (U.S. Pat. No. 7,150,744), may be used.

The inventors have found that such medicaments as described herein are optimally packaged in glass vials having a capacity of approximately 1 to 10 mL, and more preferably approximately 5 mL. Such capacities are well suited as unidose forms (i.e., single use packages) of the medicament for a variety of uses, including chemoblation of cancerous tumors via intralesional injection of the medicament. Since a preferred formulation of the medicament is not buffered, it is further preferred that such containers be made of USP Type I (low extractable or chemically resistant borosilicate) or USP Type II (low-extractable soda lime) glass, and that the inside surface of such glass containers be surface treated to reduce surface alkalinity of the container that could adversely affect medicament pH or long-term stability. Typical surface treatments applicable to such containers are described in USP<661>. The inside of such surface-treated glass containers should be rinsed with a suitable solvent, such as distilled water, one or more times prior to filling in order to remove any residue of such surface treatment. The containers should also be depyrogenated prior to filling, for example by heating to 250° C. or higher for several hours or more, and should be sterile or sterilized prior to filling using methods common in the field. It is further preferred that such containers have a minimum neck size, for example of less than 20 mm and more preferably 10 mm or less, to reduce surface area of the closures of the containers (and hence exposure of the medicament to the closures). The inventors have found that a septum-type closure, composed preferably of a pharmaceutical-grade elastomeric material with a Teflon or similar inner coating, is particularly suitable for use since it facilitates insertion of a needle into the container for withdrawal of a dose of medicament while exhibiting minimal potential for interaction with the container contents.

The present invention is not limited to the above recited examples, as other formulations familiar to those of ordinary skill in the art, including various simple or complex combinations of vehicles and adjuvants, are also useful for improving delivery of the photoactive component of the medicament to target tissues.

2. Methods and medical use of the subject medicament for chemotherapeutic treatment of conditions affecting the skin and related organs.

The medicaments disclosed herein are broadly applicable to improved chemotherapeutic treatment of various conditions affecting the skin and related organs of humans and animals. The medicament can be applied, using conventional intracorporeal or topical administration modes, directly or indirectly to, or substantially proximal to, tissues to be treated, including those of the skin, nails and scalp. Such administration modes provide direct delivery of medicament to, into or substantially proximal to, tissues to be treated, or systemic delivery of medicament to, into or substantially proximal to, tissues to be treated.

Example indications include treatment for: Psoriasis and Pustular Psoriasis; Reiter's Syndrome; Skin Ulcers, including Stasis Dermatitis, Stasis Ulcers, Ischemic Ulcers, Sickle Cell Leg Ulcers, Diabetic Ulcers, Inflammatory Ulcers; Eczematous Disease and Eczematous Reaction; various Ichthyoses; Atopic Dermatitis; Superficial Wrinkles; Near Surface Fat Reduction; Benign and Malignant Proliferative Disorders, such as Benign Epithelial Tumors and Hamartomas; Premalignant and Malignant Epithelial Tumors, including Actinic Keratoses, Basal Cell Carcinoma, Squamous Cell Carcinoma, and Keratoacanthoma; Benign and Malignant Adnexal Tumors; Tumors of Pigment-Producing Cells, including Malignant Melanoma, Solar Lentigines, Nevi, and Cafe-au-lait; Sarcomas; Lymphomas; Vascular Disorders, such as Hemangiomas and Port Wine Stain; Microbial Infection, such as Bacterial, Fungal, Yeast, Parasitic or Other Infections; Warts; and Acne. These examples are provided for illustrative purposes, as the present invention is not limited to the recited examples and includes other indications known to those skilled in the art.

3. Methods and medical use of the subject medicament for chemotherapeutic treatment of conditions affecting the mouth and digestive tract and related organs.

The medicaments disclosed herein are broadly applicable to improved chemotherapeutic treatment of various conditions affecting the mouth and digestive tract and related organs of humans and animals. The medicament can be applied, using conventional intracorporeal or topical administration modes, directly or indirectly to, or substantially proximal to, tissues to be treated, including those of the mouth, gums, tongue, larynx, pharynx, esophagus, stomach, intestines and colon. Such administration modes provide direct delivery of medicament to, into or substantially proximal to, tissues to be treated, or systemic delivery of medicament to, into or substantially proximal to, tissues to be treated.

Example indications include treatment for: Benign Esophageal Lesions, Barretts Esophagus and other Esophageal Hyperplasia and Dysplasia, and Esophageal Cancer, including Squamous Cell Carcinoma, Adenocarcinoma, Carsinosarcoma, Pseudosarcoma, and Sarcoma; Gastric Ulcers, Leiomyomas, Polyps, Neoplasms, Lymphoma and Pseudolymphoma, Adenocarcinoma, Primary Lymphoma, Leiomyosarcoma; Oral and Oropharynx Cancer and Premalignancies, Ulcers and Inflammatory Lesions, including Squamous Cell Carcinoma, Lymphoma, Actinic Cheilitis, Nicotine Stomatitis, Leukoplakia, Erythroplakia; Gum and Other Peridontal Disease, including Gingivitis; Laryngeal Hyperplasia, Dysplasia and Neoplasms; Colorectal Cancer and Polyps. These examples are provided for illustrative purposes, as the present invention is not limited to the recited examples and includes other indications known to those skilled in the art.

4. Methods and medical use of the subject medicament for chemotherapeutic treatment of conditions affecting the urinary and reproductive tracts and related organs.

The medicaments disclosed herein are broadly applicable to improved chemotherapeutic treatment of various conditions affecting the urinary and reproductive tract and related organs of humans and animals. The medicament can be applied, using conventional intracorporeal or topical administration modes, directly or indirectly to, or substantially proximal to, tissues to be treated, including those of the urethra, bladder, ureter, kidneys, vulva, vagina, cervix, uterus, fallopian tubes, ovaries, penis, testes, vas deferens, prostate, and epididymis. Such administration modes provide direct delivery of medicament to, into or substantially proximal to, tissues to be treated, or systemic delivery of medicament to, into or substantially proximal to, tissues to be treated.

Example indications include treatment for: Urinary Tract Disease, including Cancerous and Pre-Cancerous Hyperplasia, Dysplasia and Neoplasms, Tumors and other Growths, Inflammation, and Infection of the Bladder, Ureter, Urethra, and Kidney; Cancerous and Pre-Cancerous Hyperlasia, Dysplasia and Neoplasms, Tumors and other Growths, Inflammation, and Infection of the Cervix, Endometrium, Myometrium, Ovaries, Fallopian Tubes, Uterus, Vulva, and Vagina, including Vaginal Warts; Cancerous and Pre-cancerous Hyperlasia, Dysplasia and Neoplasms, Tumors and other Growths, Inflammation, and Infection of the Prostate and Testes; Cancerous and Pre-Cancerous Hyperlasia, Dysplasia and Neoplasms, Tumors and other Growths, Inflammation, and Infection of the Breast; Reproductive Tract Infections, including Tinea Cruris, Candidiasis, Condylomata Acuminata, Molluscum Contagiosum, Genital Herpes Simplex Infection, Lymphogranuloma Venereum, Chancroid, Granuloma Inguinale, Erythrasma; Psoriais; and Lichen Planus and Lichen Sclerosus. These examples are provided for illustrative purposes, as the present invention is not limited to the recited examples and includes other indications known to those skilled in the art.

5. Methods and medical use of the subject medicament for mhemotherapeutic treatment of conditions affecting the respiratory tract and related organs.

The medicaments disclosed herein are broadly applicable to improved chemotherapeutic treatment of various conditions affecting the respiratory tract and related organs of humans and animals. The medicament can be applied, using conventional intracorporeal or topical administration modes, directly or indirectly to, or substantially proximal to, tissues to be treated, including those of the lung and alveoli, bronchi, trachea, hypopharynx, larynx, nasopharynx, tear ducts, sinuses and nasal cavities. Such administration modes provide direct delivery of medicament to, into or substantially proximal to, tissues to be treated, or systemic delivery of medicament to, into or substantially proximal to, tissues to be treated.

Example indications include treatment for: Hyperplasia, Dysplasia and Neoplasia, Cancer, Inflammation and Infection of the Nasal Cavity, Paranasal Sinuses, Tear Ducts, Eustachian Tubes, Nasopharynx, Hypopharynx, Larynx, Trachea, Bronchi, Lung and Alveoli. These examples are provided for illustrative purposes, as the present invention is not limited to the recited examples and includes other indications known to those skilled in the art.

6. Methods and medical use of the subject medicament for chemotherapeutic treatment of conditions affecting the circulatory system and related organs.

The medicaments disclosed herein are broadly applicable to improved chemotherapeutic treatment of various conditions affecting the circulatory system and related organs of humans and animals. The medicament can be applied, using conventional intracorporeal or topical administration modes, directly or indirectly to, or substantially proximal to, tissues to be treated, including those of the heart, kidneys, liver and blood vessels. Such administration modes provide direct delivery of medicament to, into or substantially proximal to, tissues to be treated, or systemic delivery of medicament to, into or substantially proximal to, tissues to be treated.

Example indications include treatment for: Disease of Cardiac and Pericardial Tissues and Circulatory Tissues, including Arteries and Veins, including Plaques and Infections of such tissues, such as Bacterial Endocarditis; and destruction of unwanted blood vessels, such as spider veins. These examples are provided for illustrative purposes, as the present invention is not limited to the recited examples and includes other indications known to those skilled in the art.

7. Methods and medical use of the subject medicament for chemotherapeutic treatment of conditions affecting the head and neck.

The medicaments disclosed herein are broadly applicable to improved chemotherapeutic treatment of various conditions affecting the head and neck of humans and animals. The medicament can be applied, using conventional intracorporeal or topical administration modes, directly or indirectly to, or substantially proximal to, tissues to be treated, including those of the head, neck, brain, eyes and ears. Such administration modes provide direct delivery of medicament to, into or substantially proximal to, tissues to be treated, or systemic delivery of medicament to, into or substantially proximal to, tissues to be treated.

Example indications include treatment for: Tumors or Resected Tumor Beds of Intra-cranial and other Head and Neck Tumors; Ophthalmic Tumors and other diseases, including Macular Degeneration and Diabetic Retinopathy; Metastatic Tumors, such as Metastases of Melanoma, Breast or Other Tumors to the Skin of the Head or Neck. These examples are provided for illustrative purposes, as the present invention is not limited to the recited examples and includes other indications known to those skilled in the art.

8. Methods and medical use of the subject medicament for chemotherapeutic treatment of conditions affecting the endocrine and lymphoreticular systems and related organs.

The medicaments disclosed herein are broadly applicable to improved chemotherapeutic treatment of various conditions affecting the endocrine and lymphoreticular systems and related organs of humans and animals. The medicament can be applied, using conventional intracorporeal or topical administration modes, directly or indirectly to, or substantially proximal to, tissues to be treated, including those of the thyroid gland, the thalamus and hypothalamus, the pituitary gland, lymph nodes and lymphoreticular system. Such administration modes provide direct delivery of medicament to, into or substantially proximal to, tissues to be treated, or systemic delivery of medicament to, into or substantially proximal to, tissues to be treated.

Example indications include treatment for: Hyperplasia, Dysplasia and Neoplasia, Cancer, Inflammation and Infection of the thyroid, Thalamus and Hypothalamus, Pituitary Gland, Lymph Nodes and Lymphoreticular system, including Graves' Disease. These examples are provided for illustrative purposes, as the present invention is not limited to the recited examples and includes other indications known to those skilled in the art.

9. Methods and medical use of the subject medicament for chemotherapeutic treatment of conditions affecting various other tissues, such as connective tissues and various tissue surfaces exposed during surgery.

The medicaments disclosed herein are broadly applicable to improved chemotherapeutic treatment of various conditions affecting various other internal or external tissues of humans and animals, such as connective tissues and various tissue surfaces that become exposed during surgery. The medicament can be applied, using conventional intracorporeal or topical administration modes, directly or indirectly to, or substantially proximal to, tissues to be treated, including those of tissue surfaces exposed during surgery, including endoscopic surgery or other endoscopic procedures. Such application modes provide direct delivery of medicament to, into or substantially proximal to, tissues to be treated, or systemic delivery of medicament to, into or substantially proximal to, tissues to be treated.

Example indications include treatment for: Joint Inflammation, such as that of Arthritis; Resected Tumor Beds of Thoracic, Abdominal, or other Tumors; Metastatic Tumors, such as Metastases of Breast Tumors to the Skin; Tumors or Infections of the Pleura, Peritoneum or Pericardium; and various other substantially similar indications. These examples are provided for illustrative purposes, as the present invention is not limited to the recited examples and includes other indications known to those skilled in the art.

10. Methods and medical use of the subject medicament for chemotherapeutic treatment of conditions related to microbial, viral, fungal or parasitic infection.

The medicaments disclosed herein are broadly applicable to improved chemotherapeutic treatment of various conditions related to microbial, viral, fungal or parasitic infection of humans and animals. The medicament can be applied, using conventional intracorporeal or topical administration modes, directly or indirectly to, or substantially proximal to, tissues to be treated, including those of tissue surfaces exposed during surgery, including endoscopic surgery or other endoscopic procedures. Such administration modes provide direct delivery of medicament to, into or substantially proximal to, tissues to be treated, or systemic delivery of medicament to, into or substantially proximal to, tissues to be treated.

Example indications include treatment for: Bacterial and Antibiotic Resistant Bacterial Infection, including those caused by Gram Positives and Gram Negatives, *Streptomycetes*, Actinomycetes, Staphylococci, Streptococci, *Pseudomonas, Escherichia coli, Mycobacteria* and others; Infection caused by Filamentous Fungi and Non-filamentous Fungi like *Cryptosporidium, Histoplasma, Aspergillus, Blastomyces, Candida* and others; Parasitic Infection caused by Amoeba (including for use in lysing and killing amoeba in amoebic cysts), *Trichinella*, Dirodfilaria (Heart worm in dogs) and various other substantially similar indications. These examples are provided for illustrative purposes, as the present invention is not limited to the recited examples and includes other indications known to those skilled in the art.

11. Additional Properties of the Claimed Medicaments

Details defining parameters such as composition of the claimed medicaments, methods of administration, and directions for usage should be consistent with relevant U.S. federal and international regulations (such as those promulgated by the International Conference on Harmonization, ICH) covering pharmaceutical products. Such regulations, including those promulgated by the U.S. Food and Drug Administration ("FDA") in Title 21 of the Code of Federal Regulations (CFR), strictly regulate medical products within the jurisdictional territories of the respective regulatory agencies. Among other parameters, such regulations define specific features of any such medical product, and in particular certain aspects of the manufacturing and labeling of such medical products. Accordingly, such features are an inherent element of the medicaments described herein. Particularly relevant features relate to identification of the medicament and directions for its usage (i.e., product labeling).

For instance, the FDA has detailed labeling requirements concerning the recital of ingredients and directions for use for any medical product sold in interstate commerce. These requirements are enumerated in Title 21, Section 201, Subpart A ("General Labeling Provisions") of the CFR. For example, 21 CFR §201.5 ("Drugs; adequate directions for use") requires detailed labeling concerning intended use and dosage:

"Adequate directions for use means directions under which the layman can use a drug safely and for the purposes for which it is intended. (Section 201.128 defines "intended use.") Directions for use may be inadequate because, among other reasons, of omission, in whole or in part, or incorrect specification of:

(a) Statements of all conditions, purposes, or uses for which such drug is intended, including conditions, purposes, or uses for which it is prescribed, recommended, or suggested in its oral, written, printed, or graphic advertising, and conditions, purposes, or uses for which the drug is commonly used; except that such statements shall not refer to conditions, uses, or purposes for which the drug can be safely used only under the supervision of a practitioner licensed by law and for which it is advertised solely to such practitioner.

(b) Quantity of dose, including usual quantities for each of the uses for which it is intended and usual quantities for persons of different ages and different physical conditions.

(c) Frequency of administration or application.

(d) Duration of administration or application.

(e) Time of administration or application (in relation to time of meals, time of onset of symptoms, or other time factors).

(f) Route or method of administration or application.

(g) Preparation for use, i.e., shaking, dilution, adjustment of temperature, or, other manipulation or process."

Thus, the FDA mandates labeling that makes intended use clear even to the layman. Moreover, the FDA also strictly regulates the quantitative, definitive identification of drug ingredients; 21 CFR §201.10 ("Drugs; statement of ingredients") states:

"(a) The ingredient information . . . shall appear together, without any intervening written, printed, or graphic matter, . . .

(b) The term ingredient applies to any substance in the drug, whether added to the formulation as a single substance or in admixture with other substances . . . "

Accordingly, at an absolute minimum, all medicaments and pharmaceutical compositions must bear detailed marking (i.e., labeling) describing use and composition.

Subpart B ("Labeling Requirements from Prescription Drugs") of Section 201 codifies unique features required of all prescription medicaments and pharmaceutical preparations, as illustrated by the following passages:

"21 CFR §201.56 (General requirements on content and format of labeling for human prescription drugs)

"Prescription drug labeling . . . shall contain the information in the format required by §201.57 and shall meet the following general requirements:

(d)(1) The labeling shall contain specific information . . . under the following section headings and in the following order:

Description.
Clinical Pharmacology.
Indications and Usage.
Contraindications.
Warnings.
Precautions.
Adverse Reactions.
Drug Abuse and Dependence.
Overdosage.
Dosage and Administration.
How Supplied."

Section 201.57 ("Specific requirements on content and format of labeling for human prescription drugs") expands on these enumerated requirements, stating, for example, that the labeling of a prescription product shall contain the following description:

"(i) The proprietary name and the established name, if any of the drug;

(ii) The type of dosage form and the route of administration to which the labeling applies;

(iii) The same qualitative and/or quantitative ingredient information as required under §201.100(b) for labels;

(iv) If the product is sterile, a statement of that fact;

(v) The pharmacological or therapeutic class of the drug;

(vi) The chemical name and structural formula of the drug;

(vii) If the product is radioactive, a statement of the important nuclear physical characteristics, such as the principal radiation emission data, external radiation, and physical decay characteristics.

(2) If appropriate, other important chemical or physical information, such as physical constants, or pH, shall be stated."

Subsequent passages in this section define labeling for indications and usage, for dosage and administration, and for the other parameters identified in section 201.56, supra.

Subpart C ("Labeling Requirements for Over-the-Counter Drugs", §§201.61-201.66) codifies similar requirements for non-prescription medicaments and pharmaceutical preparations, while Subpart D ("Exemptions from Adequate Directions for Use", §§201.100-201.129) defines similar requirements for experimental products as well as bulk packages intended for distribution through pharmacies and similar channels.

Finally, concerning intended use for a drug, section 201.128 ("Meaning of 'intended uses'") states:

"The words intended uses or words of similar import . . . refer to the objective intent of the persons legally responsible for the labeling of drugs. The intent is determined by such persons' expressions or may be shown by the circumstances surrounding the distribution of the article. This objective intent may, for example, be shown by labeling claims, advertising matter, or oral or written statements by such persons or their representatives."

Thus, intended use must be conveyed on the label of all pharmaceutical products, in all product advertising, and in any other statements about the product.

These federal regulations make it clear that any drug product, such as the presently claimed medicament, is, within all jurisdictions of the U.S., strictly regulated by the FDA, and must include detailed labeling concerning composition and intended use.

The manufacturer is legally responsible for assuring compliance with these FDA requirements.

As such, these requirements assure that the commercial channels for any medicament such as those of the present application are clearly distinct from other non-pharmaceutical products, including those that might include Rose Bengal or another halogenated xanthene. Furthermore, the medicaments of the present application are clearly distinct from other pharmaceutical products that include Rose Bengal or another halogenated xanthene, provided that the other pharmaceutical products have a different formulation (dosage form), route of administration or indication (intended use) from that of the medicaments of the present application.

This distinction is illustrated by experience of the inventors, who are undertaking development of two products, (1) a topical photodynamic medicament for treatment of psoriasis and (2) an injectable chemotherapeutic medicament for treatment of cancer, both of which contain Rose Bengal as their active component. These two medicaments are the subject of separate investigational new drug applications (IND's) with the FDA. If successful in their respective clinical trials, they will become the subject of separate new drug applications (NDA's). And ultimately, if they are approved by the FDA for commercial sale, they will be assigned distinct approval numbers indicative of the fact that they are distinct pharmaceutical products. Similarly, if the inventors were to elect to undertake clinical development of an intracorporeal photodynamic medicament, this would require filing of another IND and NDA since this third product would encompass a separate dosage form, route of administration, and intended use compared with either the topical photodynamic medicament or the injectable chemotherapeutic medicament.

Thus, any pharmaceutical product, including prescription or over-the-counter medicaments based on this disclosure, that are to be introduced into commerce in the U.S. or any other jurisdiction conforming to ICH standards, must contain certain elements, including proper labeling concerning intended use, that differentiates such product from any other product, despite any superficial similarities to such other product. Thus, such a pharmaceutical product is not defined simply by its active ingredient, but rather by the combination of active ingredients and labeling claims (including intended use and dosage form). For example, an injectable medicament (dosage form) for chemotherapeutic ablation of cancerous tumors (intended use) containing rose bengal (active ingredient) is not rose bengal but rather a distinct pharmaceutical product containing rose bengal.

TABLE I

Physical Properties of Fluorescein and Some Example Halogenated Xanthenes.

| Compound | Substitution | | | | | MW (g) |
|---|---|---|---|---|---|---|
| | X | Y | Z | $R^1$ | $R^2$ | |
| Fluorescein | H | H | H | Na | Na | 376 |
| 4',5'-Dichlorofluorescein | Cl | H | H | Na | Na | 445 |
| 2',7'-Dichlorofluorescein | H | Cl | H | Na | Na | 445 |
| 4,5,6,7-Tetrachlorofluorescein | H | H | Cl | H | H | 470 |
| 2',4',5',7'-Tetrachlorofluorescein | Cl | Cl | H | Na | Na | 514 |
| Dibromofluorescein | Br | H | H | Na | Na | 534 |
| Solvent Red 72 | H | Br | H | H | H | 490 |
| Diiodofluorescein | I | H | H | Na | Na | 628 |
| Eosin B | $NO_2$ | Br | H | Na | Na | 624 |
| Eosin Y | Br | Br | H | Na | Na | 692 |
| Ethyl Eosin | Br | Br | H | $C_2H_5$ | K | 714 |
| Erythrosin B | I | I | H | Na | Na | 880 |
| Phloxine B | Br | Br | Cl | Na | Na | 830 |
| Rose Bengal | I | I | Cl | Na | Na | 1018 |
| 4,5,6,7-Tetrabromoerythrosin | I | I | Br | Na | Na | 1195 |

TABLE 2

Partition coefficients and toxicology data for several halogenated xanthenes (i.e. Rose Bengal, Erythrosin B and Phloxine B) and selected other therapeutic agents. Partition coefficient, $K_p$, is the ratio of equilibrium concentrations of agent in a lipophilic phase (n-octanol) contacted with an aqueous phase (phosphate buffered saline, PBS, pH = 7.4). Toxicology data ($LD_{50}$) for murine intravenous (i.v.) or oral (p.o.) administration.

| Agent | $K_p$ | $LD_{50}$ (mg/kg) | |
|---|---|---|---|
| | | i.v. | p.o. |
| Phloxine B | 1.1 | 310 | 310 |
| Erythrosin B | 1.9 | 370 | >1,000 |
| Rose Bengal | 11.5 | | >1,000 |
| Indocyanine Green | 99 | 60 | |
| Porphyrin HpIX | 1.5 | | >1,000 |

This description has been offered for illustrative purposes only and is not intended to limit the invention of this application.

What is claimed as new and desired to be protected by Letters Patent is set forth in the appended claims.

We claim:

1. A medicament adapted for intralesional injection, the medicament consisting of:
a hydrophilic vehicle containing a halogenated xanthene having a structure of Formula I

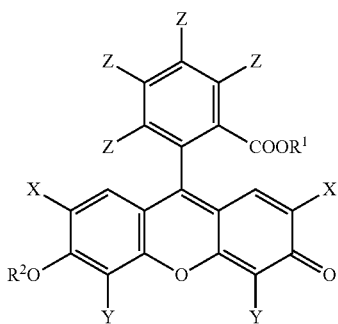

Formula I wherein X is selected from the group consisting of hydride, bromide, chloride, and iodide, Y is selected from the group consisting of hydride, bromide, chloride, and iodide, and Z is selected from the group consisting of hydride, bromide, and chloride, such that said halogenated xanthene is Rose Bengal, wherein said halogenated xanthene is at a concentration in the range of from 1% to 20%, wherein $R^1$ is an ion selected from the group consisting of hydrogen ion ($H^+$) and sodium ion ($Na^+$), and $R^2$ is an ion selected from the group consisting of hydrogen ion ($H^+$) and sodium ion ($Na^+$), said halogenated xanthene being dissolved in said vehicle at a concentration of from greater than 1% to less than 20%; and an electrolyte consisting of sodium chloride; wherein the electrolyte is present in said vehicle at a concentration of 0.1-2%, or wherein the electrolyte is present in said vehicle at a level sufficient to provide an osmolality of the medicament of greater than 100 mOsm/kg, said medicament having a pH in the range from 4 to 10, and wherein:

said medicament is sterile;

said medicament contains pyrogenic material at a level of no more than 10 Endotoxin Units per mL;

said medicament contains particulate material at a level of no more than 300 particles of size 25 microns or larger and no more than 3000 particles of size 10 microns or larger;

and said medicament includes labeling in conformance with International Conference on Harmonization standards specifying that said medicament is for injection.

2. The medicament of claim 1 wherein said halogenated xanthene is at a concentration of 10%.

3. The medicament of claim 1 wherein said pH is in the range from 5 to 9.

4. The medicament of claim 1 wherein said pH is in the range from 6 to 8.

5. The medicament of claim 1 wherein said electrolyte is at a concentration of 0.5-1.5%.

6. The medicament of claim 1 wherein said electrolyte is at a concentration of 0.8-1.2%.

7. The medicament of claim 1 wherein said electrolyte is at a concentration of 0.9%.

8. The medicament of claim 1 wherein the osmolality of the medicament is greater than 250 mOsm/kg.

9. The medicament of claim 1 wherein the osmolality of the medicament is in the range of 300-500 mOsm/kg.

10. The medicament of claim 1 wherein said hydrophilic vehicle consists of water.

11. The medicament of claim 1 wherein said medicament includes directions for usage as an injectable medicament for chemotherapeutic treatment of diseased human tissue.

12. The medicament of claim 1 wherein said labeling includes directions for usage as an injectable medicament for chemotherapeutic treatment of cancer.

13. The medicament of claim 1 wherein said labeling includes directions for usage as an injectable medicament for chemoablation of cancer.

14. The medicament of claim 1 wherein said labeling specifies the dosage form as an injectable medicament, the intended use as chemotherapy, and the active ingredient as Rose Bengal.

15. The medicament of claim 1 wherein said labeling specifies the dosage form as an injectable medicament, the intended use as chemoablation of cancer, and the active ingredient as Rose Bengal.

16. The medicament of claim 1 wherein said medicament is packaged in a USP Type I or Type II glass vial.

17. The medicament of claim 16 wherein said glass vial has been surface coated as specified in USP <661>.

18. The medicament of claim 16 wherein said glass vial has been depyrogenated at a temperature of 250° C. or greater prior to filling with said medicament.

19. The medicament of claim 16 wherein said glass vial contains from 1 to 10 mL of said medicament.

20. The medicament of claim 16 wherein said glass vial contains 5 mL of said medicament.

* * * * *